United States Patent [19]
Kuhnt et al.

[11] Patent Number: 5,276,008
[45] Date of Patent: Jan. 4, 1994

[54] SUBSTITUTED 4,5-DIAMINO-1,2,4-TRIAZOL-3-(THI)ONES

[75] Inventors: Dietmar Kuhnt; Kurt Findeisen, both of Leverkusen; Michael Haug, Bergisch Gladbach; Joachim Kluth, Langenfeld; Klaus-Helmut Müller, Duesseldorf; Klaus König, Odenthal; Thomas Himmler, Cologne; Gunther Beck; Hans-Joachim Santel, both of Leverkusen; Klaus Lürssen, Bergisch Gladbach; Robert R. Schmidt, Bergisch Gladbach; Birgit Krauskopf, Bergisch Gladbach, all of Fed. Rep. of Germany

[73] Assignee: Bayer Aktiengesellschaft, Leverkusen, Fed. Rep. of Germany

[21] Appl. No.: 831,261

[22] Filed: Jan. 31, 1992

Related U.S. Application Data

[60] Continuation-in-part of Ser. No. 764,437, Sep. 23, 1991, Pat. No. 5,220,032, which is a division of Ser. No. 565,293, Aug. 9, 1990, Pat. No. 5,082,490.

[30] Foreign Application Priority Data

Feb. 7, 1991 [DE] Fed. Rep. of Germany ....... 4103700

[51] Int. Cl.$^5$ .................. A01N 43/653; C07D 249/12
[52] U.S. Cl. ................................. 504/273; 548/263.8
[58] Field of Search ........................ 71/92; 548/263.8; 504/273

[56] References Cited
U.S. PATENT DOCUMENTS
5,082,490  1/1992  Muller et al. ................... 548/263.8

Primary Examiner—Patricia L. Morris
Attorney, Agent, or Firm—Sprung Horn Kramer & Woods

[57] ABSTRACT

The invention relates to new substituted 4,5-diamino-1,2,4-triazol-3-(thi)ones of the general formula (I),

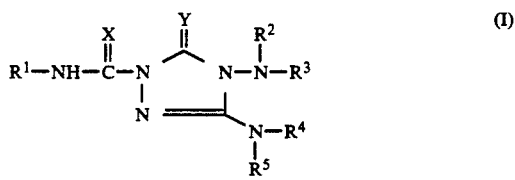

in which
R$^1$ represents alkyl, alkenyl, alkinyl, halogenoalkyl, halogenoalkenyl, halogenoalkinyl, cyanoalkyl, hydroxyalkyl, alkoxyalkyl, aryloxyalkyl, arylthioalkyl, arylsulfinylalkyl, arylsulfonylalkyl, arylaminoalkyl, N-alkyl-arylaminoalkyl, alkoxycarbonylalkyl, alkoxycarbonylalkenyl, alkylaminoalkyl, dialkylaminoalkyl, in each case optionally substituted cycloalkyl, cycloalkylalkyl, cycloalkenyl or cycloalkenylalkyl, or optionally substituted heterocyclylalkyl, or in each case optionally substituted aralkyl, arylalkenyl, arylalkinyl, aroyl, aryl, aralkyloxy or aryloxy, for alkoxy, alkenyloxy or alkinyloxy, R$^2$, R$^3$, R$^4$ and R$^5$ are identical or different and independently of one another represent hydrogen, alkyl, alkenyl, alkinyl, halogenoalkyl, halogenoalkenyl, halogenoalkinyl, cyanoalkyl, alkoxyalkyl, alkylthioalkyl, in each case optionally substituted cycloalkyl, cycloalkylalkyl, aryl or aralkyl or in each case two of these radicals (R$^2$ and R$^3$ or R$^4$ and R$^5$) represent together alkanediyl and R$^5$ can also represent alkoxy, X represents oxygen or sulphur and
Y represents oxygen or sulphur, a plurality of processes and new intermediates for their preparation, and their use as herbicides and plant growth regulators.

11 Claims, No Drawings

SUBSTITUTED 4,5-DIAMINO-1,2,4-TRIAZOL-3-(THI)ONES

This is a continuation-in-part of application Ser. No. 764,437, filed Sep. 23, 1991, now U.S. Pat. No. 5,220,032, which is a division of application Ser. No. 565,293, filed Aug. 9, 1980, now U.S. Pat. No. 5,082,490.

The invention relates to new, substituted 4,5-diamino-1,2,4-triazol-3-(thi)ones, a plurality of processes and new intermediates for their preparation, and their use as herbicides and plant growth regulators.

It has been disclosed that certain substituted triazolones, such as, for example, 4-amino-5-methyl-2-phenylaminocarbonyl-2,4-dihydro-3H-1,2,4-triazol-3-one, have herbicidal properties (cf. EP-A 294,666). However, the herbicidal action of this known compound is not satisfactory in all respects.

New, substituted 4,5-diamino-1,2,4-triazol-3-(thi)ones have now been found of the general formula (I)

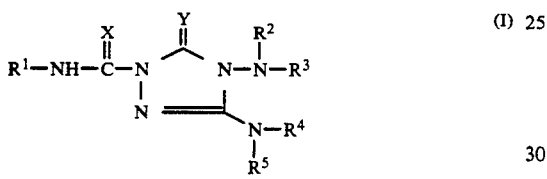

in which
$R^1$ represents alkyl, alkenyl, alkinyl, halogenoalkyl, halogenoalkenyl, halogenoalkinyl, cyanoalkyl, hydroxyalkyl, alkoxyalkyl, aryloxyalkyl, arylthioalkyl, arylsulphinylalkyl, arylsulphonylalkyl, arylaminoalkyl, N-alkyl-arylaminoalkyl, alkoxycarbonylalkyl, alkoxycarbonylalkenyl, alkylaminoalkyl, dialkylaminoalkyl, or in each case optionally substituted cycloalkyl, cycloalkylalkyl, cycloalkenyl or cycloalkenylalkyl, or optionally substituted heterocyclylalkyl, or in each case optionally substituted aralkyl, arylalkenyl, arylalkinyl, aroyl, aryl, aralkyloxy or aryloxy, or alkoxy, alkenyloxy or alkinyloxy, $R^2$, $R^3$, $R^4$ and $R^5$ are identical or different and independently of one another represent hydrogen, alkyl, alkenyl, alkinyl, halogenoalkyl, halogenoalkenyl, halogenoalkinyl, cyanoalkyl, alkoxyalkyl, alkylthioalkyl, or in each case optionally substituted cycloalkyl, cycloalkylalkyl, aryl or aralkyl, or in each case two of these radicals ($R^2$ and $R^3$ or $R^4$ and $R^5$) together represent alkanediyl, and $R^5$ can also represent alkoxy, X represents oxygen or sulphur and
Y represents oxygen or sulphur.

The compounds of the formula (I), depending on the nature of the substituents $R^1$, $R^2$, $R^3$, $R^4$ and $R^5$, can optionally be present as geometrical and/or optical isomers or isomer mixtures of differing composition. Both the pure isomers and the isomer mixtures are claimed according to the invention.

It has further been found that the new substituted 4,5-diamino-1,2,4-triazol-3-(thi)ones of the general formula (I)

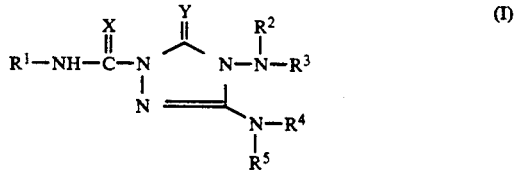

in which
$R^1$ represents alkyl, alkenyl, alkinyl, halogenoalkyl, halogenoalkenyl, halogenoalkinyl, cyanoalkyl, hydroxyalkyl, alkoxyalkyl, aryloxyalkyl, arylthioalkyl, arylsulphinylalkyl, arylsulphonylalkyl, arylaminoalkyl, N-alkyl-arylaminoalkyl, alkoxycarbonylalkyl, alkoxycarbonylalkenyl, alkylaminoalkyl, dialkylaminoalkyl, or in each case optionally substituted cycloalkyl, cycloalkylalkyl, cycloalkenyl or cycloalkenylalkyl, or optionally substituted heterocyclylalkyl, or in each case optionally substituted aralkyl, arylalkenyl, arylalkinyl, aroyl, aryl, aralkyloxy or aryloxy, or alkoxy, alkenyloxy or alkinyloxy, $R^2$, $R^3$, $R^4$ and $R^5$ are identical or different and independently of one another represent hydrogen, alkyl, alkenyl, alkinyl, halogenoalkyl, halogenoalkenyl, halogenoalkinyl, cyanoalkyl, alkoxyalkyl, alkylthioalkyl, or in each case optionally substituted cycloalkyl, cycloalkylalkyl, aryl or aralkyl, or in each case two of these radicals ($R^2$ and $R^3$ or $R^4$ and $R^5$) together represent alkanediyl, and $R^5$ can also represent alkoxy, X represents oxygen or sulphur and
Y represents oxygen or sulphur, are obtained when (a) 4,5-diamino-1,2,4-triazol-3-(thi)ones of the general formula (II)

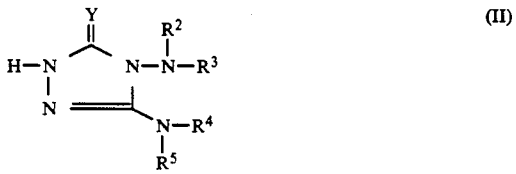

in which
$R^2$, $R^3$, $R^4$, $R^5$ and Y have the abovementioned meanings, are reacted with iso(thio)cyanates of the general formula (III)

$$R^1-N=C=X \qquad (III)$$

in which
$R^1$ and X have the abovementioned meanings, if appropriate in the presence of a diluent and if appropriate in the presence of a reaction auxiliary, or when (b) 4-alkylideneamino-5-amino-1,2,4-triazol-3-(thi)ones of the general formula (IV)

in which

R$^1$, R$^4$, R$^5$, X and Y have the abovementioned meanings and

R$^6$ and R$^7$ are identical or different and independently of one another represent hydrogen, alkyl, aralkyl or aryl, are reacted with aqueous acids, if appropriate in the presence of organic solvents, or when (c) substituted 1,2,4-triazol-3-(thi)ones of the general formula (V)

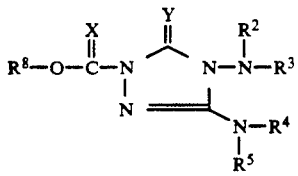

in which

R$^2$, R$^3$, R$^4$, R$^5$, X and Y have the abovementioned meanings and

R$^8$ represents alkyl, aralkyl or aryl, are reacted with amino compounds of the general formula (VI)

in which

R$^1$ has the abovementioned meaning if appropriate in the presence of a diluent and if appropriate in the presence of a reaction auxiliary, or when (d) 4,5-diamino-1,2,4-triazol-3-(thio)ones of the general formula (II)

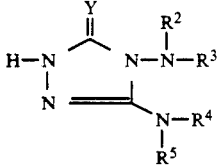

in which

R$^2$, R$^3$, R$^4$, R$^5$ and Y have the abovementioned meanings, are reacted with (thio)urethanes of the general formula (VII)

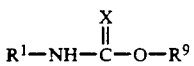

in which

R$^1$ and X have the abovementioned meanings and

R$^9$ represents alkyl, aralkyl or aryl, if appropriate in the presence of a diluent and if appropriate in the presence of a reaction auxiliary, or when (e) 4-oxyalkylideneamino-5-amino-1,2,4-triazol-3-(thi)-ones of the general formula (VIII)

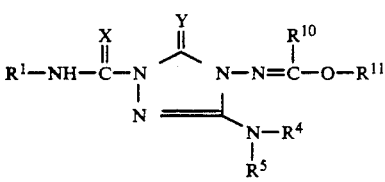

in which

R$^1$, R$^4$, R$^5$, X and Y have the abovementioned meanings and

R$^{10}$ and R$^{11}$ are identical or different and independently of one another represent alkyl, alkenyl, alkinyl, cycloalkyl, aralkyl or aryl, and R$^{10}$ also represents hydrogen, are reacted with hydride complexes of the general formula (IX)

$$M^1M^2H_4 \quad (IX)$$

in which

M$^1$ represents lithium, sodium or potassium and

M$^2$ represents boron or aluminum, if appropriate in the presence of a diluent, or when (f) 4-alkylideneamino-5-amino-1,2,4-triazol-3-(thi)ones of the general formula (IV)

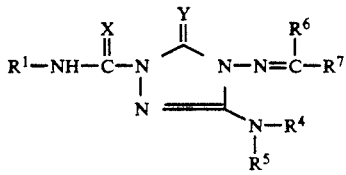

in which

R$^1$, R$^4$, R$^5$, X and Y have the abovementioned meanings and

R$^6$ and R$^7$ are identical or different and independently of one another represent hydrogen, alkyl, aralkyl or aryl, are reacted with reducing agents, if appropriate in the presence of catalysts and if appropriate in the presence of diluents.

Finally, it has been found that the new substituted 4,5-diamino-1,2,4-triazol-3-ones of the general formula (I) have interesting herbicidal properties.

Surprisingly, the substituted 4,5-diamino-1,2,4-triazol-3-ones of the general formula (I) show considerably stronger herbicidal action against problem weeds than the compound 4-amino-5-methyl-2-phenylaminocarbonyl-2,4-dihydro-3H-1,2,4-triazol-3-one, which is closely terms of structure and profile of action.

In the definitions, the aromatic radicals such as, for example, aryl, aryloxy or aralkyl preferably represent phenyl or naphthyl, in particular phenyl. The aliphatic carbon chains, even if it is not expressly indicated, are in each case straight-chain or branched.

The substituent heterocyclylalkyl in R$^1$ preferably denotes heterocyclylalkyl having 1 to 6 carbon atoms in the straight-chain or branched alkyl moiety and 2 to 9 carbon atoms and also 1 to 3 heteroatoms—in particular nitrogen, oxygen and/or sulphur—in the heterocyclyl moiety, where the heterocyclyl moiety can be monosubstituted or polysubstituted, in particular monosubstituted, disubstituted or trisubstituted, by identical or different halogen, cyano, nitro and C$_1$-C$_5$-alkyl, C$_1$-C$_5$-alkoxy, C$_1$-C$_5$-alkylthio, halogeno-C$_1$-C$_5$-alkyl, halogeno-C$_1$-C$_5$-alkoxy, halogeno-C$_1$-C$_5$-alkylthio or C$_1$-C$_5$-alkoxycarbonyl. The heterocyclyl moiety can in particular be substituted by fluorine, chlorine, cyano, nitro, methyl, ethyl, n- or i-propyl, n-, i-, s- or t-butyl, methoxy, ethoxy, methylthio, trifluoromethyl, trifluoromethoxy or trifluoromethylthio. Particularly preferably, the substituent heterocyclylalkyl in R$^1$ represents heterocyclylmethyl, heterocyclylpropyl or heterocyclylethyl which are optionally monosubstituted to trisubstituted in the heterocyclyl moiety by identical or different substituents, suitable heterocycles in each case being:

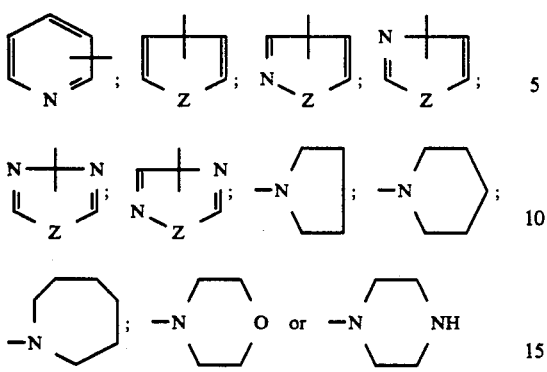

where Z in each case represents oxygen or sulphur and in each case suitable substituents being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio.

Formula (I) provides a general definition of the substituted 4,5-diamino-1,2,4-triazol-3-(thi)ones according to the invention. Preferred compounds of the formula (I) are those in which R$^1$ represents in each case straight-chain or branched alkyl having 1 to 18 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl or halogenoalkinyl in each case having 2 to 8 carbon atoms and 1 to 15 or 1 to 13 identical or different halogen atoms respectively, cyanoalkyl having 1 to 8 carbon atoms, hydroxyalkyl having 1 to 8 carbon atoms and 1 to 6 hydroxyl groups, or phenoxyalkyl, phenylthioalkyl, phenylsulphinylalkyl, phenylsulphonylalkyl, phenylaminoalkyl or N-($C_1$-$C_4$-alkyl)-phenylaminoalkyl in each case having 1 to 4 carbon atoms in the alkyl moiety, alkoxyalkyl, alkoxycarbonylalkyl or alkoxycarbonylalkenyl in each case having 1 to 6 carbon atoms in the individual alkyl and alkenyl moieties, alkylaminoalkyl or dialkylaminoalkyl in each case having 1 to 6 carbon atoms in the individual alkyl moieties, or cycloalkyl, cycloalkylalkyl, cycloalkenyl or cycloalkenylalkyl in each case having 3 to 8 carbon atoms in the cycloalkyl or cycloalkenyl moiety and if appropriate 1 to 6 carbon atoms in the alkyl moiety and in each case optionally monosubstituted to trisubstituted by identical or different substituents, suitable substituents in each case being: halogen, cyano, phenyl, cyclohexyl, phenylethyl, phenylisopropyl and in each case straight-chain or branched alkyl or halogenoalkyl in each case having 1 to 4 carbon atoms and if appropriate 1 to 9 identical or different halogen atoms and straight-chain or branched halogenoalkenyl having 1 to 4 carbon atoms and 1 to 5 identical or different halogen atoms or in each case doubly linked alkanediyl, or alkenediyl in each case having up to 4 carbon atoms; R additionally represents heterocyclylalkyl having 1 to 6 carbon atoms in the straight-chain or branched alkyl moiety and 2 to 9 carbon atoms and also 1 to 3 heteroatoms—in particular nitrogen, oxygen and/or sulphur—in the heterocyclyl moiety and optionally monosubstituted or polysubstituted in the heterocyclyl moiety by identical or different substituents, suitable substituents being: halogen, cyano, nitro, and also in each case straight-chain or branched alkyl, alkoxy, alkylthio, halogenoalkyl, halogenoalkoxy, halogenoalkylthio or alkoxycarbonyl in each case having 1 to 5 carbon atoms and if appropriate 1 to 9 identical or different halogen atoms; R$^1$ additionally represents in each case straight-chain or branched alkoxy having 1 to 8 carbon atoms, alkenyloxy having 2 to 8 carbon atoms or alkinyloxy having 2 to 8 carbon atoms or represents aralkyl, arylalkenyl, arylalkinyl, aroyl, aryl, aralkyloxy or aryloxy, in each case having 6 to 10 carbon atoms in the aryl moiety and if appropriate 1 to 8 carbon atoms in the straight-chain or branched alkyl moiety or 2 to 8 carbon atoms in the straight-chain or branched alkenyl moiety or alkinyl moiety and in each case optionally monosubstituted to trisubstituted by identical or different substituents, it being possible for the hydrogen atoms of the α-carbon atom to be replaced by ethane-1,2-diyl, propane-1,3-diyl, butane-1,4-diyl or pentane-1,5-diyl and suitable alkyl substituents optionally being halogen and cyano and suitable aryl substituents in each case being: halogen, cyano, nitro, amino, hydroxyl, in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl in each case having 1 to 6 carbon atoms in the alkyl moiety and if appropriate 1 to 9 identical or different halogen atoms, cycloalkyl having 3 to 6 carbon atoms and phenoxy; or R: represents benzyl having an —O—CH$_2$—O— group fused to the phenyl moiety, R$^2$, R$^3$, R$^4$ and R$^5$ are identical or different and independently of one another represent hydrogen, or in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogeno-alkenyl or halogenoalkinyl in each case having 2 to 8 carbon atoms and 1 to 15 or 1 to 13 identical or different halogen atoms respectively, cyanoalkyl having 1 to 8 carbon atoms, alkoxyalkyl or alkylthioalkyl in each case having up to 4 carbon atoms in the individual alkyl moieties, or cycloalkyl or cycloalkylalkyl in each case having 3 to 8 carbon atoms in the cycloalkyl moiety and if appropriate 1 to 6 carbon atoms in the alkyl moiety and in each case optionally monosubstituted to trisubstituted by identical or different substituents, suitable substituents in each case being: halogen, cyano and in each case straight-chain or branched alkyl or halogenoalkyl in each case having 1 to 4 carbon atoms and if appropriate 1 to 9 identical or different halogen atoms, the radicals R$^2$ to R$^5$ further represent aryl or aralkyl in each case having 6 or 10 carbon atoms in the aryl moiety and if appropriate 1 to 4 carbon atoms in the straight-chain or branched alkyl moiety and in each case optionally monosubstituted to trisubstituted by identical or different substituents, suitable substituents being: halogen, cyano, nitro, hydroxyl, in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl in each case having 1 to 6 carbon atoms in the alkyl moiety and if appropriate 1 to 9 halogen atoms, in which additionally two of these radicals in each case—$R^2$ and $R^3$ or $R^4$ and $R^5$—can also together represent straight-chain or branched alkanediyl having 2 to 6 carbon atoms, and $R^5$ can also represent straight-chain or branched alkoxy having 1 to 8 carbon atoms, X represents oxygen or sulphur and Y represents oxygen or sulphur.

Particularly preferred compounds of the formula (I) are those in which $R^1$ represents methyl, ethyl, n- or i-propyl, n-, i-, s- or t-butyl, in each case straight-chain or branched pentyl, hexyl, heptyl, octyl, nonyl, decyl, dodecyl, or allyl, in each case straight-chain or branched butenyl, pentenyl or hexenyl, propargyl, in each case straight-chain or branched butinyl, pentinyl or hexinyl, or straight-chain or branched halogenoalkyl having 1 to 8 carbon atoms and 1 to 9 identical or different halogen atoms, in particular fluorine, chlorine or bromine, or in each case straight-chain or branched halogenoalkenyl or halogenoalkinyl in each case having 3 to 8 carbon atoms and 1 to 3 halogen atoms, in particular fluorine or chlorine, or in each case straight-chain or branched cyanoalkyl having 1 to 6 carbon atoms in the alkyl moiety, hydroxyalkyl having 1 to 6 carbon atoms and 1 to 3 hydroxyl groups, alkoxyalkyl, alkoxycarbonylalkyl or alkoxycarbonylalkenyl, alkylaminoalkyl or dialkylaminoalkyl in each case having up to 4 carbon atoms in the individual alkyl or alkenyl moieties or represents cyclopropyl, cyclopropylmethyl, cyclopropylethyl, cyclopentyl, cyclohexyl, cycloheptyl, cyclooctyl, cyclohexylmethyl, cyclohexylethyl, cyclohexenyl or cyclohexenylmethyl which are in each case optionally monosubstituted to trisubstituted by identical or different substituents, suitable substituents in each case being: fluorine, chlorine, bromine, methyl, ethyl, n- or i-propyl, n-, i-, s- or t-butyl, cyano, methanediyl, ethanediyl, butanediyl or butadienediyl or dichloroallyl;

$R^1$ furthermore represents heterocyclylmethyl, heterocyclylpropyl or heterocyclylethyl which are optionally monosubstituted to trisubstituted in the heterocyclyl moiety by identical or different substituents, suitable heterocycles in each case being:

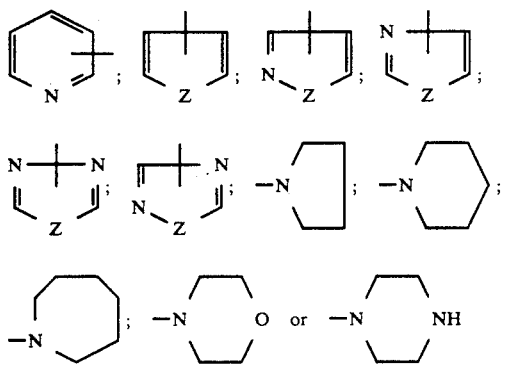

where Z in each case represents oxygen or sulphur and suitable substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or tri-fluoromethylthio;

$R^1$ additionally represents in each case straight-chain or branched alkoxy having 1 to 6 carbon atoms, alkenyloxy having 3 to 6 carbon atoms or alkinyloxy having 3 to 6 carbon atoms or represents in each case optionally straight-chain or branched benzyl, phenylethyl, phenylpropyl, phenylpropenyl, phenylpropinyl, phenylbutyl, phenylbutenyl, phenylbutinyl, phenylpentyl, phenylpentenyl, phenylpentinyl, phenylhexyl, phenylhexenyl, phenylhexinyl, phenylheptyl, phenylheptenyl, phenylheptinyl, phenyloctyl, phenyloctenyl, phenyloctinyl, phenylcyanomethyl, phenylcyanoethyl, phenylcyanopropyl, benzyloxy, phenylethyloxy, phenoxy, phenoxyethyl, phenoxypropyl, phenoxy-i-propyl, phenoxyisobutyl, phenoxy-tert-butyl, phenylthioisobutyl, phenylthiotert-butyl, phenylthioethyl, phenylthiopropyl, phenylthio-i-propyl, benzoyl, phenyl or naphthyl which are in each case optionally monosubstituted to trisubstituted by identical or different substituents, suitable phenyl substituents in each case being: fluorine, chlorine, bromine, hydroxyl, cyano, nitro, methyl, ethyl, n- or i-propyl, n-, i-, s- or t-butyl, methoxy, ethoxy, methylthio, difluoromethyl, trifluoromethyl, difluoromethoxy, trifluoromethoxy, trifluoromethylthio, trifluoro-methylsulphinyl, trifluoromethylsulphonyl, methyl-sulphinyl, methylsulphonyl, acetyl, propionyl, methoxycarbonyl, ethoxycarbonyl, n- or i-propoxy-carbonyl, cyclohexyl or phenoxy, $R^2$ represents hydrogen, methyl, ethyl, propyl, isopropyl, butyl, isobutyl, sec-butyl, allyl, propargyl, cyanoethyl, methoxyethyl, cyclopropyl, cyclopentyl, cyclohexyl, phenyl or benzyl, $R^3$ represents hydrogen, methyl, ethyl, propyl, butyl, allyl, propargyl, cyanoethyl, methoxyethyl or benzyl which is optionally substituted by chlorine, or together with $R^2$ represents butane-1,4-diyl or pentane-1,5-diyl, $R^4$ represents hydrogen, methyl, ethyl, propyl, isopropyl, butyl, isobutyl, sec-butyl, allyl, propargyl, cyanoethyl, methoxyethyl, cyclopropyl, cyclopentyl, cyclohexyl, phenyl or benzyl, $R^5$ represents hydrogen, methyl, ethyl, propyl, butyl, allyl, propargyl, cyanoethyl, methoxyethyl, methoxy or benzyl, or together with $R^4$ represents butane-1,4-diyl or pentane-1,5-diyl, X represents oxygen or sulphur and Y represents oxygen or sulphur.

Very particularly preferred compounds of the formula (I) are those in which $R^1$ represents 1-methyl-3-phenyl-propyl, 1-ethyl-3-phenyl-propyl, 1-propyl-3-phenyl-propyl, 1-isopropyl-3-phenyl-propyl, 2-methyl-3-phenyl-propyl, 1,1-dimethyl-3-phenyl-propyl, 1-methyl-1-ethyl-3-phenyl-propyl, 1,1-diethyl-3-phenyl-propyl, 1-methyl-1-propyl-3-phenyl-propyl, 1-methyl-3-phenyl-2-propenyl, 1-ethyl-3-phenyl-2-propenyl, 1-propyl-3-phenyl-2-propenyl, 1-isopropyl-3-phenyl-2-propenyl, 1,1-dimethyl-3-phenyl-2-propenyl, 1-methyl-1-ethyl-3-phenyl-2-propenyl, 1,1-diethyl-3-phenyl-2-propenyl, 1-methyl-1-propyl-3-phenyl-2-propenyl, 1-methyl-3-phenyl-2-propinyl, 1-ethyl- 3-phenyl-2-propinyl, 1-propyl-3-phenyl-2-propinyl, 1-isopropyl-3-phenyl-2-propinyl, 1,1-dimethyl-3-phenyl-2-propinyl, 1-methyl-1-ethyl-3-phenyl-2-propinyl, 1,1-diethyl-3-phenyl-2-propinyl, 1-methyl-1-propyl-3-phenyl-2-propinyl, 1,2-dimethyl-3-phenylpropyl, 2-ethyl-1-methyl-3-phenyl-propyl, 1,2,2-trimethyl-3-phenyl-propyl, 1,3,3-trimethyl-3-phenylpropyl or 1,1,2,2-tetramethyl-3-phenyl-propyl which are in each case optionally monosubstituted to trisubstituted by identical or different substituents, suitable phenyl substituents in each case being: fluorine, chlorine, bromine, methyl, ethyl, n- or i-propyl, n-, i-, s- or t-butyl, trifluoromethyl, phenyl, methoxy, ethoxy, propoxy, isopropoxy, difluoromethoxy, trifluoromethoxy, difluoromethyl, methoxycarbonyl, ethoxycarbonyl, propoxycarbonyl, cyano, methylthio, ethylthio, propylthio, isopropylthio, difluoromethylthio, trifluoromethylthio, methylsulphinyl, methylsulphonyl and trifluoromethylsulphonyl, furthermore $R^2$ represents hydrogen, $R^3$ represents hydrogen or methyl, $R^4$ represents hydrogen, methyl or ethyl, $R^5$ represents hydrogen, methyl, ethyl, n- or iso-propyl, or $R^4$ and $R^5$ together represent butane-1,4-diyl, X represents oxygen or sulphur and Y represents oxygen.

If, for example, 4-methylamino-5-dimethylamino-2,4-dihydro-3H-1,2,4-triazol-3-one and 1-methyl-3-phenyl-propyl isocyanate are used as starting substances, the course of the reaction in process (a) according to the invention can be represented by the following equation:

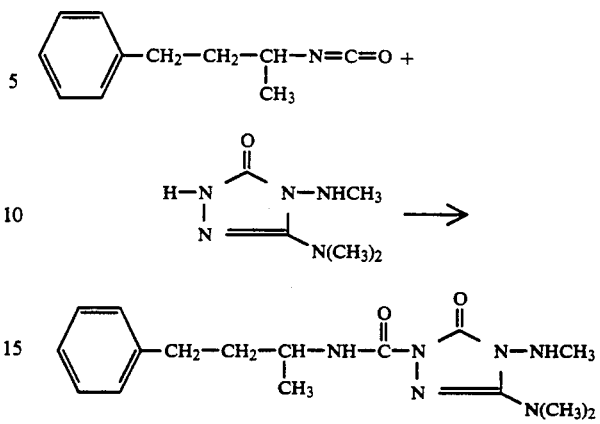

If, for example, 2-(1-methyl-3-phenyl-2-propinyl-aminocarbonyl)-4-isopropylideneamino-5-dipropylamino-2,4-dihydro-3H-1,2,4-triazol-3-one is used as a starting substance, the course of the reaction in process (b) according to the invention can be represented by the following equation:

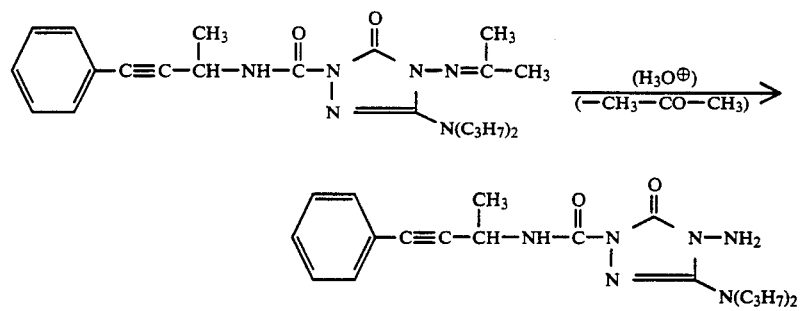

If, for example, 2-phenoxycarbonyl-4-methylamino-5-(N-methyl-propylamino)-2,4-dihydro-3H-1,2,4-triazol-3-one and 1,1-dimethyl-3-(4-methyl-phenyl)-propylamine are used as starting substances, the course of the reaction in process (c) according to the invention can be represented by the following equation:

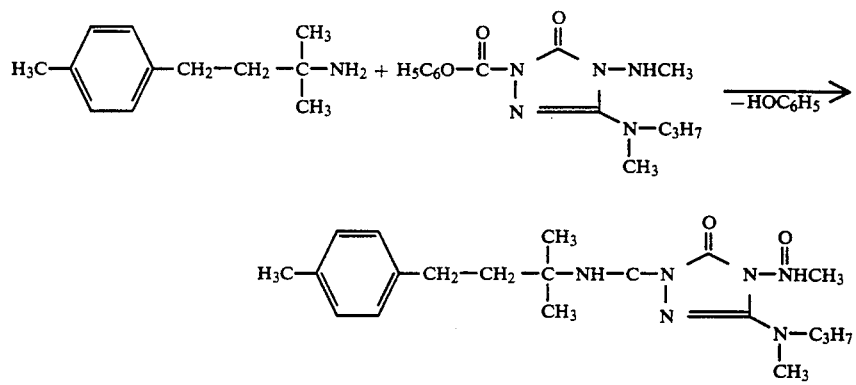

If, for example, 4-dimethylamino-5-diethylamino-2,4-dihydro-3H-1,2,4-triazol-3-one and N-(1-methyl-3-phenyl-2-propenyl)-O-phenyl-urethane are used as starting substances, the course of the reaction in process (d) according to the invention can be represented by the following equation:

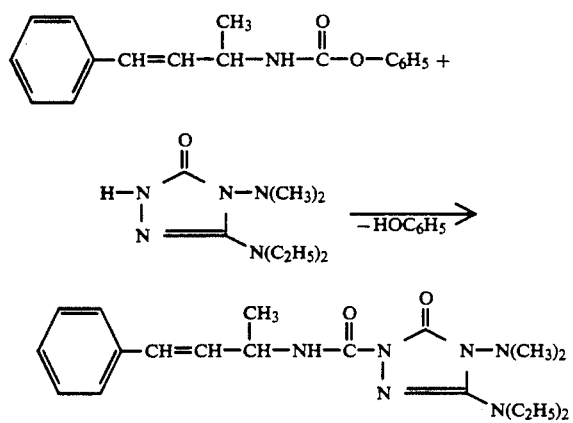

If, for example, 2-(1,1-dimethyl-3-phenyl-propylaminocarbonyl)-4-ethoxymethyleneamino-5-(pyrrolidin-1-yl)-2,4-dihydro-3H-1,2,4-triazol-3-one and sodium borohydride are used as starting substances, the course of the reaction in process (e) according to the invention can be represented by the following equation:

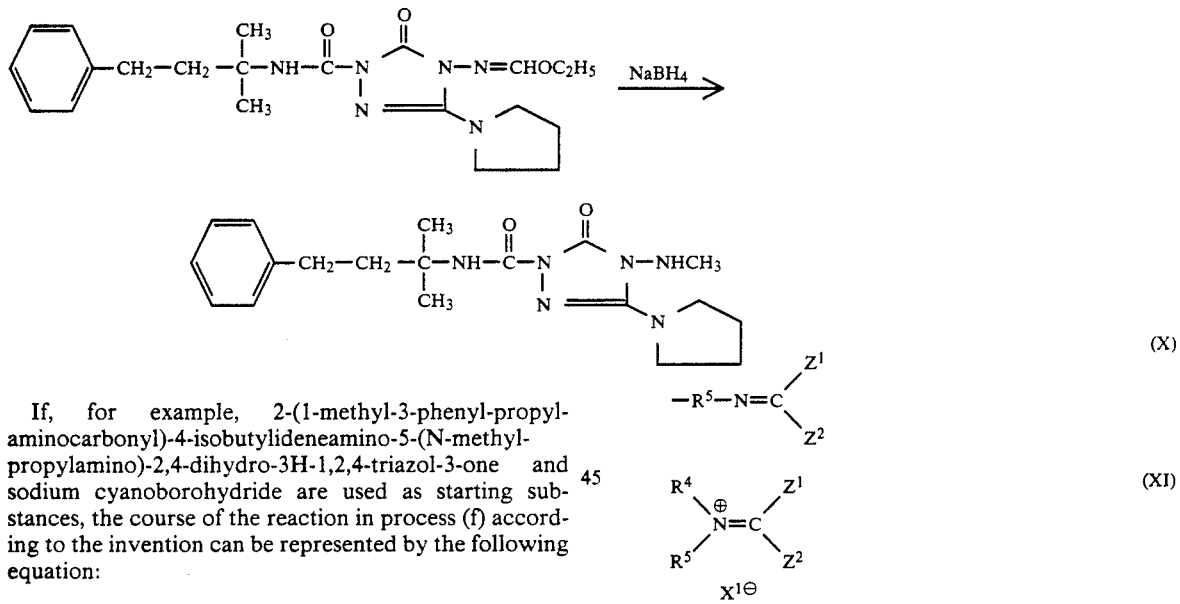

If, for example, 2-(1-methyl-3-phenyl-propyl-aminocarbonyl)-4-isobutylideneamino-5-(N-methyl-propylamino)-2,4-dihydro-3H-1,2,4-triazol-3-one and sodium cyanoborohydride are used as starting substances, the course of the reaction in process (f) according to the invention can be represented by the following equation:

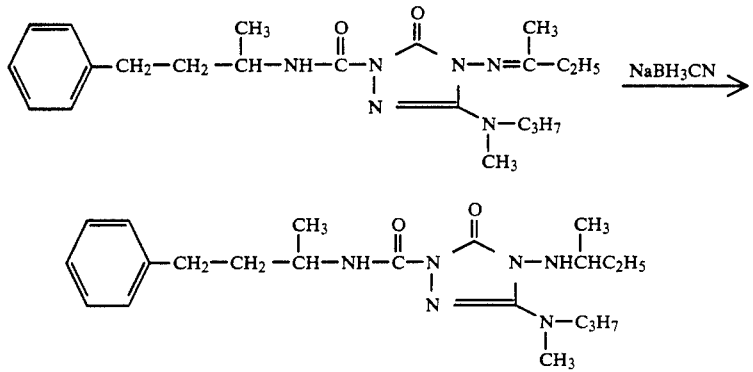

Formula (II) provides a general definition of the 4,5-diamino-1,2,4-triazol-3-ones to be used as starting substances in processes (a) and (d) according to the inven-tion for the preparation of compounds of the formula (I).

In formula (II), $R^2$, $R^3$, $R^4$, $R^5$ and Y preferably or in particular have those meanings which have already been indicated above preferably or as particularly preferred for $R^2$, $R^3$, $R^4$, $R^5$ and Y in connection with the description of the compounds of the formula (I) according to the invention.

The 4,5-diamino-1,2,4-triazol-3-(thi)ones of the formula (II) are known and/or can be prepared by processes known per se (cf. Advan. Heterocycl. Chem. 5 (1965), 119-204; Chem. Ber. 99 (1966), 81-84; J. Chem. Soc. 1952, 4817; J. Heterocycl. Chem. 2 (1965), 302-304; Eur. J. Med. Chem.—Chim. Ther. 21 (1986), 235-244; J. Chem. Soc. C 1968, 2099-2107; J. Chem. Soc. C 1970, 26-34; Liebigs Ann. Chem. 702 (1967), 101-111; Liebigs Ann. Chem. 703 (1967), 116-130; preparation examples).

The compounds of the formula (II) are obtained, for example, when (α) amino or imino compounds of the general formulae (X), (XI) or (XII)

$$-R^5-N=C\begin{matrix}Z^1\\Z^2\end{matrix} \qquad (X)$$

$$\begin{matrix}R^4\\ \\R^5\end{matrix}\overset{\oplus}{N}=C\begin{matrix}Z^1\\Z^2\end{matrix} \qquad (XI)$$

$$X^{\ominus}$$

-continued

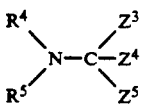
(XII)

in which
R⁴ and R⁵ have the abovementioned meanings,
X¹ represents halogen and
Z¹, Z², Z³, Z⁴ and Z⁵ represent leaving groups customary in carbonic acid chemistry, are reacted with carbodihydrazide derivatives of the general formulae (XIIIa) or (XIIIb)

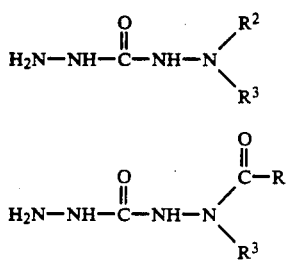

(XIIIa)

(XIIIb)

in which
R² and R³ have the abovementioned meanings and
R represents alkyl, alkoxy or aryl, if appropriate in the presence of a diluent, such as, for example, phenol and/or chlorobenzene, if appropriate in the presence of a catalyst, such as, for example, dibutyltin oxide, and if appropriate in the presence of an acid acceptor, such as, for example, sodium carbonate, at temperatures between 20° C. and 200° C., the grouping —CO—R is then optionally eliminated at temperatures between 20° C. and 120° C. by reaction with an aqueous alkali, such as, for example, sodium hydroxide solution and the mixture is worked up by customary methods (cf. the preparation examples), or when (β) diaminoguanidine derivatives of the general formula (XIV)

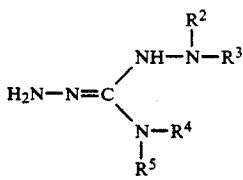
(XIV)

in which
R², R³, R⁴ and R⁵ have the abovementioned meanings, or acid adducts of compounds of the formula (XIV) or tautomers of compounds of the formula (XIV) are reacted with carbonic acid derivatives of the general formula (XV)

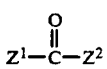
(XV)

in which
Z¹ and Z² have the abovementioned meanings, if appropriate in the presence of a diluent, such as, for example, phenol, and if appropriate in the presence of an acid acceptor, such as, for example, sodium carbonate, at temperatures between 20° C. and 200° C. and the mixture is worked up by customary methods (cf. the preparation examples).

In the formulae (X), (XI) and (XII), R⁴ and R⁵ preferably or in particular have those meanings which have already been indicated above as preferred or as particularly preferred for R⁴ and R⁵ in the description of the compounds of the formula (IIa) and Z¹, Z², Z³, Z⁴ and Z⁵ are identical or different and preferably represent halogen, C₁-C₄-alkoxy, C₁-C₄-alkylthio, C₁-C₄-alkylamino, di-(C₁-C₂-alkyl)-amino, phenoxy or phenylthio, in particular chlorine, methoxy, ethoxy, methylthio, ethylthio, methylamino, ethylamino, dimethylamino or phenoxy.

The leaving groups from the series Z¹ to Z⁵ may optionally also be linked. Z¹ and Z² or Z³ and Z⁴ then preferably together represent C₂-C₄-alkanedioxy, in particular ethan-1,2-dioxy (—OCH₂CH₂O—).

The compounds of the formulae (X), (XI) and (XII) are known and/or can be prepared by processes known per se (cf. Synthesis 1977, 73–90; loc. cit. 1988, 460–466; J. Chem. Soc. 1951, 2492–2494; Chem. Ber. 120 (1987), 339–344; Tetrahedron Lett. 1982, 3539–3542; Houben-Weyl, Methoden der Organischen Chemie (Methods of Organic Chemistry), 4th Edition, Volume E4 (1983), 522–624 and 652–722).

In the formulae (XIIIa) and (XIIIb), R² and R³ preferably or in particular have those meanings which have already been indicated above as preferred or as particularly preferred for R² and R³ in the description of the compounds of the formula (IIa) and R preferably represents C₁-C₄-alkyl, C₁-C₄-alkoxy or phenyl, in particular methyl, ethyl, methoxy or ethoxy.

The carbodihydrazide derivatives of the formula (XIIIa) are, with the exception of carbodihydrazide (R²=R³=H), still unknown from the literature.

The new compounds of the formula (XIIIa) are obtained when carbonic acid derivatives of the formula (XV)

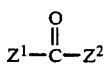
(XV)

in which
Z¹ and Z² have the abovementioned meanings, are reacted successively with about one mol equivalent of a hydrazine derivative of the formula (XVI)

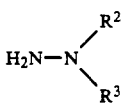
(XVI)

in which
R² and R³ have the abovementioned meanings and about one mol equivalent of hydrazine or hydrazine hydrate at temperatures between 0° C. and 100° C. Working up can then be carried out by customary methods. Preferably, however, the compounds of the formula (XIIIa) are not isolated in pure form, but directly further reacted.

The new compounds of the formula (XIIIb) are obtained when hydrazine derivatives of the formula (XVIa)

$$H_2N-N\begin{smallmatrix}H\\ \diagup\\ \diagdown\\ R^3\end{smallmatrix} \quad \text{(XVIa)}$$

in which

R³ has the abovementioned meaning, are reacted with acylating agents of the formula (XVII)

$$X^2-\underset{\underset{\text{O}}{\|}}{C}-R \quad \text{(XVII)}$$

in which

R has the abovementioned meaning and

X² represents halogen or the group —O—CO—R, if appropriate in the presence of a diluent, such as, for example, methanol, methylene chloride or toluene, and if appropriate in the presence of an acid acceptor, such as, for example, potassium carbonate or pyridine, at temperatures between −80° C. and +80° C., the acylated hydrazines obtained in this reaction of the general formula (XVIII)

$$H_2N-N\begin{smallmatrix}\underset{\|}{C}-R\\ \diagup\quad\text{O}\\ \diagdown\\ R^3\end{smallmatrix} \quad \text{(XVIII)}$$

in which

R³ and R have the abovementioned meanings, are reacted with carbonic acid derivatives of the general formula (XV)

$$Z^1-\underset{\underset{\text{O}}{\|}}{C}-Z^2 \quad \text{(XV)}$$

in which

Z¹ and Z² have the abovementioned meanings, if appropriate in the presence of a diluent, such as, for example, methylene chloride or ethylene chloride, and if appropriate in the presence of an acid acceptor, such as, for example, sodium carbonate, at temperatures between −20° C. and +80° C. and the doubly acylated hydrazines obtained in this reaction of the formula (XIX)

$$Z^2-\underset{\underset{\text{O}}{\|}}{C}-NH-N\begin{smallmatrix}\underset{\|}{C}-R\\ \diagup\quad\text{O}\\ \diagdown\\ R^3\end{smallmatrix} \quad \text{(XIX)}$$

in which

R³, R and Z² have the abovementioned meanings, are reacted with hydrazine or hydrazine hydrate, if appropriate in the presence of a diluent, such as, for example, chlorobenzene, at temperatures between 0° C. and 120° C. (cf. the preparation examples).

The compounds of the formulae (XV), (XVI), (XVIa) and (XVII) needed as precursors are known chemicals for organic synthesis.

In the formula (XIV), R², R³, R⁴ and R⁵ preferably or in particular have those meanings which have already been indicated above as preferred or as particularly preferred for R², R³, R⁴ and R⁵ in the description of the compounds of the formula (IIa).

The compounds of the formula (XIV) are known and/or can be prepared by processes known per se (cf. EP-A 150,677).

In the formula (XV), $Z^1$ and $Z^2$ are identical or different and each preferably represent halogen, $C_1-C_4$-alkoxy, $C_1-C_4$-alkylthio, $C_1-C_4$-alkylamino, di-($C_1-C_2$-alkyl)-amino, phenoxy or phenylthio, in particular chlorine, methoxy, ethoxy, phenoxy, methylthio or dimethylamino. $Z^1$ and $Z^2$ can also be linked in cyclic fashion. $Z^1$ and $Z^2$ then preferably together represent $C_2-C_4$-alkanedioxy, in particular ethane-1,2-dioxy (—OCH₂CH₂O—). The compounds of the formula (XV) are known chemicals for organic synthesis.

Formula (III) provides a general definition of the iso(thio)cyanates further to be used as starting substances in process (a) according to the invention.

In formula (III), R¹ and X preferably or in particular have those meanings which have already been indicated above preferably or as particularly preferred for R¹ and X in connection with the description of the compounds of the formula (I) according to the invention.

The iso(thio)cyanates of the formula (III) are largely known chemicals for organic synthesis (cf., for example, Nouv. J. Chim. 1 (1977), 243-254—cited in Chem. Abstracts 87: 151614a; Liebigs Ann. Chem. 562 (1949), 75-136).

The iso(thio)cyanates which are new and a subject of the present application are those of the formula (III) in which R¹ represents 1-ethyl-3-phenyl-propyl, 1-propyl-3-phenyl-propyl, 1-isopropyl-3-phenyl-propyl, 2-methyl-3-phenyl-propyl, 1,1-dimethyl-3-phenyl-propyl, 1,2-dimethyl-3-phenyl-propyl, 1,1-diethyl-3-phenyl-propyl, 1-methyl-1-propyl-3-phenyl-propyl, 1,2,2-trimethyl-3-phenyl-propyl, 1-methyl-3-phenyl-2-propenyl, 1-ethyl-3-phenyl-2-propenyl, 1-propyl-3-phenyl-2-propenyl, 1-isopropyl-3-phenyl-2-propenyl, 1,1-dimethyl-3-phenyl-2-propenyl, 1-methyl-1-ethyl-3-phenyl-2-propenyl, 1,1-diethyl-3-phenyl-2-propenyl, 1-methyl-1-propyl-3-phenyl-2-propenyl, 1-methyl-3-phenyl-2-propinyl, 1-ethyl-3-phenyl-2-propinyl, 1-propyl-3-phenyl-2-propinyl, 1-isopropyl-3-phenyl-2-propinyl, 1,1-dimethyl-3-phenyl-2-propinyl, 1-methyl-1-ethyl-3-phenyl-2-propinyl, 1,1-diethyl-3-phenyl-2-propinyl, 1-methyl-1-propyl-3-phenyl-2-propinyl, 1,2-dimethyl-3-phenylpropyl, 2-ethyl-1-methyl-3-phenyl-propyl, 1,2,2-trimethyl-3-phenyl-propyl, 1,3,3-trimethyl-3-phenylpropyl or 1,1,2,2-tetramethyl-3-phenyl-propyl which are in each case optionally monosubstituted to tri-substituted by identical or different substituents, suitable phenyl substituents in each case being: fluorine, chlorine, bromine, methyl, ethyl, n- or i-propyl, n-, i-, s- or t-butyl, trifluoromethyl, phenyl, methoxy, ethoxy, propoxy, isopropoxy, difluoromethoxy, trifluoromethoxy, difluoromethyl, methoxycarbonyl, ethoxycarbonyl, propoxycarbonyl, cyano, methylthio, ethylthio, propylthio, isopropylthio, difluoromethylthio, trifluoromethylthio, methylsulphinyl, methylsulphonyl and trifluoromethylsulphonyl and X represents oxygen or sulphur, preferably oxygen.

The new iso(thio)cyanates of the formula (III) are obtained when amino compounds of the general formula (VI)

$$R^1-NH_2 \quad \text{(VI)}$$

in which

R[1] represents 1-ethyl-3-phenyl-propyl, 1-propyl-3-phenyl-propyl, 1-isopropyl-3-phenyl-propyl, 2-methyl-3-phenyl-propyl, 1,1-dimethyl-3-phenyl-propyl, 1,2-dimethyl-3-phenyl-propyl, 1,1-diethyl-3-phenyl-propyl, 1-methyl-1-propyl-3-phenyl-propyl, 1,2,2-trimethyl-3-phenyl-propyl, 1-methyl-3-phenyl-2-propenyl, 1-ethyl-3-phenyl-2-propenyl, 1-propyl-3-phenyl-2-propenyl, 1-isopropyl-3-phenyl-2-propenyl, 1,1-dimethyl-3-phenyl-2-propenyl, 1-methyl-1-ethyl-3-phenyl-2-propenyl, 1,1-diethyl-3-phenyl-2-propenyl, 1-methyl-1-propyl-3-phenyl-2-propenyl, 1-methyl-3-phenyl-2-propinyl, 1-ethyl-3-phenyl-2-propinyl, 1-propyl-3-phenyl-2-propinyl, 1-isopropyl-3-phenyl-2-propinyl, 1,1-dimethyl-3-phenyl-2-propinyl, 1-methyl-1-ethyl-3-phenyl-2-propinyl, 1,1-diethyl-3-phenyl-2-propinyl or 1-methyl-1-propyl-3-phenyl-2-propinyl, 1,2-dimethyl-3-phenyl-propyl, 2-ethyl-1-methyl-3-phenyl-propyl, 1,2,2-trimethyl-3-phenyl-propyl, 1,3,3-trimethyl-3-phenyl-propyl or 1,1,2,2-tetramethyl-3-phenylpropyl, which are in each case optionally monosubstituted to trisubstituted by identical or different substituents, suitable phenyl substituents in each case being: fluorine, chlorine, bromine, methyl, ethyl, n- or i-propyl, n-, i-, s- or t-butyl, trifluoromethyl, phenyl, methoxy, ethoxy, propoxy, isopropoxy, difluoromethoxy, trifluoromethoxy, difluoromethyl, methoxycarbonyl, ethoxycarbonyl, propoxycarbonyl, cyano, methylthio, ethylthio, propylthio, isopropylthio, difluoromethylthio, trifluoromethylthio, methylsulphinyl, methylsulphonyl and trifluoromethylsulphonyl, are reacted with phosgene, if appropriate in the presence of a diluent, such as, for example, toluene or chlorobenzene, at temperatures between 0° C. and 150° C. (cf. the preparation examples), or when the amino compounds of the formula (VI) indicated as starting substances are reacted with thiophosgene, if appropriate in the presence of diluents, such as, for example, toluene or chloroform and water, at temperatures between −10° C. and +50° C.

The starting substances of the formula (VI) needed in this case are further discussed below in connection with the description of process (c) according to the invention.

Formula (IV) provides a general definition of the 4-alkylideneamino-5-amino-1,2,4-triazol-3-(thi)ones to be used as starting substances in processes (b) and (f) according to the invention for the preparation of compounds of the formula (I).

In formula (IV), $R^1$, $R^4$, $R^5$, X and Y preferably or in particular have those meanings which have already been indicated above preferably or as particularly preferred for $R^1$, $R^4$, $R^5$, X and Y in connection with the description of the compounds of the formula (I) according to the invention and $R^6$ and $R^7$ preferably in each case independently of one another represent hydrogen, straight-chain or branched alkyl having 1 to 4 carbon atoms, phenyl or benzyl.

The compounds of the formula (IV) are obtained, for example, when the 4,5-diamino-1,2,4-triazol-3-(thi)ones described above of the general formula (II)

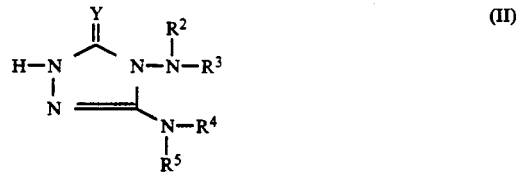

in which $R^2$, $R^3$, $R^4$, $R^5$ and Y have the abovementioned meanings, with the proviso that $R^2$ and $R^3$ represent hydrogen, are reacted with aldehydes or ketones of the formula (XX)

in which $R^6$ and $R^7$ have the abovementioned meanings, if appropriate in the presence of a diluent, such as, for example, methylene chloride or toluene, and if appropriate in the presence of a catalyst, such as, for example, p-toluenesulphonic acid, at temperatures between 20° C. and 120° C. and the 4-alkylideneamino-5-amino-1,2,4-triazol-3-(thi)ones thus obtained of the formula (XXI)

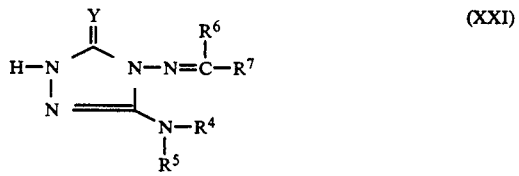

in which $R^4$, $R^5$, $R^6$, $R^7$ and Y have the abovementioned meanings, are either reacted in a subsequent second step with iso(thio)cyanates of the formula (III)

in which $R^1$ and X have the abovementioned meanings, if appropriate in the presence of a diluent, such as, for example, methylene chloride or dioxane, and if appropriate in the presence of a reaction auxiliary, such as, for example, triethylamine, at temperatures between 20° C. and 150° C., or when the compounds of the formula (XXI) are alternatively reacted in a second step with chloro(thio)formic acid esters of the formula (XXII)

in which

X has the abovementioned meaning and $R^8$ represents alkyl, aryl or aralkyl, if appropriate in the presence of a diluent, such as, for example, tetrahydrofuran, and if appropriate in the presence of a reaction auxiliary, such as, for example, sodium hydride or potassium tert-butoxide, at temperatures between −20° C. and the 2-oxy(thio)-carbonyl-4-alkylideneamino-5-amino-1,2,4-triazol-3-(thi)ones thus obtained of the formula (XXIII)

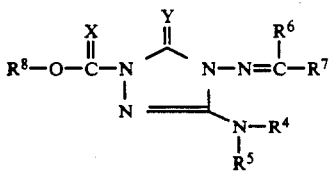

in which
R$^4$, R$^5$, R$^6$, R$^7$, R$^8$, X and Y have the abovementioned meanings, are reacted in a subsequent third step with amines of the formula (VI)

R$^1$—NH$_2$ (VI)

in which
R$^1$ has the abovementioned meaning, if appropriate in the presence of a diluent, such as, for example, tetrahydrofuran or dioxane, and if appropriate in the presence of a base, such as, for example, sodium hydroxide or potassium hydroxide, at temperatures between 20° C. and 100° C.

It is possible and may be advantageous in this case to carry out the reaction of the compounds of (XXI) with chloro(thio)formic acid esters and the subsequent reaction with amines in so-called one-pot processes.

The aldehydes or ketones of the formula (XX), the iso(thio)cyanates of the formula (III), the chloro(thio)formic acid esters of the formula (XXII) and the amines of the formula (VI) are largely known chemicals for organic synthesis.

Formula (V) provides a general definition of the substituted 1,2,4-triazol-3-(thi)ones to be used as starting substances in process (c) according to the invention for the preparation of compounds of the formula (I).

In formula (V), R$^2$, R$^3$, R$^4$, R$^5$, X and Y preferably or in particular have those meanings which have already been indicated above preferably or as particularly preferred for R$^2$, R$^3$, R$^4$, R$^5$, X and Y in connection with the description of the compounds of the formula (I) according to the invention, and R$^8$ preferably represents methyl, ethyl, propyl, isopropyl, butyl, isobutyl, sec-butyl, tert-butyl, phenyl or benzyl.

The compounds of the formula (V) are obtained, for example, when 4,5-diamino-1,2,4-triazol-3-(thi)ones of the formula (II)

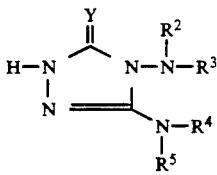

in which
R$^2$, R$^3$, R$^4$, R$^5$ and Y have the abovementioned meanings, are reacted with chloro(thio)formic acid esters of the formula (XXII)

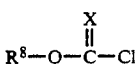

in which
R$^8$ and X have the abovementioned meanings, if appropriate in the presence of a diluent, such as, for example, tetrahydrofuran, and if appropriate in the presence of a acid acceptor, such as, fir example, potassium tert-butoxide, at temperatures between −20° C. and +100° C.

Formula (VI) provides a general definition of the amino compounds further to be used as starting substances in process (c) according to the invention.

In formula (VI), R$^1$ preferably or in particular has that meaning which has already been indicated above preferably or as particularly preferred for R$^1$ in connection with the description of the compounds of the formula (I) according to the invention.

The starting substances of the formula (VI) are known and/or can be prepared by processes known per se (cf. J. Med. Chem. 25 (1982), 1363-1370; Tetrahedron Lett. 29 (1988), 223-224; Chem. Ber. 117 (1984), 856-858; DE-OS (German Published Specification) 3,426,919; EP-A-237,305; J. Am. Chem. Soc. 71 (1949), 3482-3485; Tetrahedron Lett. 27 (1986), 3957-3960; Bull. Soc. Chim. France 1974 (3-4, Pt. 2), 615-622; Tetrahedron Lett. 31 (1990), 2661-2664; J. Med. Chem. 13 (1970), 1249-1250; preparation examples).

Formula (VII) provides a general definition of the (thio)urethanes to be used as starting substances in process (d) according to the invention for the preparation of compounds of the formula (I).

In formula (VII), R$^1$ and X preferably or in particular have those meanings which have already been indicated above preferably or as particularly preferred for R: and X in connection with the description of the compounds of the formula (I) according to the invention and R$^9$ preferably represents methyl, ethyl, propyl, isopropyl, butyl, isobutyl, sec-butyl, tert-butyl, phenyl or benzyl.

The starting substances of the formula (VII) are largely known chemicals for organic synthesis.

Formula (VIII) provides a general definition of the 4-oxyalkylideneamino-5-amino-1,2,4-triazol(thi)ones to be used as starting substances in process (e) according to the invention for the preparation of compounds of the formula (I).

In formula (VIII), R$^1$, R$^4$, R$^5$, X and Y preferably or in particular have those meanings which have already been indicated above preferably or as particularly preferred for R$^1$, R$^4$, R$^5$, X and Y in connection with the description of the compounds of the formula (I) according to the invention and R$^{10}$ and R$^{11}$ preferably represent hydrogen, C$_1$-C$_6$-alkyl, C$_2$-C$_6$-alkenyl, C$_2$-C$_6$-alkinyl, C$_3$-C$_6$-cycloalkyl, phenyl or benzyl.

R$^{10}$ in particular represents hydrogen, methyl, ethyl, propyl, phenyl or benzyl and R$^{11}$ represents methyl, ethyl, propyl or benzyl.

The compounds of the formula (VIII) are obtained, for example, when 4,5-diamino-1,2,4-triazol-3-(thi)ones of the general formula (II)

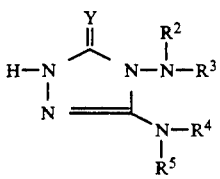

in which
R$^2$ and R$^3$ represent hydrogen and

Y, $R^4$ and $R^5$ have the abovementioned meanings, are reacted with orthocarboxylic acid esters of the general formula (XXIV)

$$R^{10}-C(OR^{11})_3 \quad (XXIV)$$

in which $R^{10}$ and $R^{11}$ have the abovementioned meanings, if appropriate in the presence of a diluent, such as, for example, chloroform, toluene or chlorobenzene, and if appropriate in the presence of a catalyst, such as, for example, p-toluenesulphonic acid, at temperatures between 50° C. and 200° C. and the oxyalkylidene compounds thus obtained of the formula (XXV)

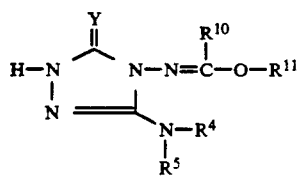

in which $R^4$, $R^5$, $R^{10}$, $R^{11}$ and Y have the abovementioned meanings, are reacted in a subsequent second step with iso(thio)-cyanates of the formula (III)

$$R^1-N=C=X \quad (III)$$

in which $R^1$ and X have the abovementioned meanings, if appropriate in the presence of a diluent, such as, for example, methylene chloride or dioxane, and if appropriate in the presence of a reaction auxiliary, such as, for example, triethylamine, at temperatures between 20° C. and 150° C.

Alternatively, the compounds of the formula (VIII) are also obtained when compounds of the formula (I)

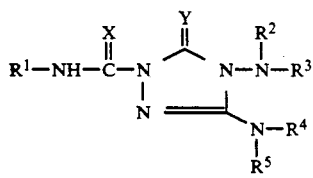

in which $R^2$ and $R^3$ represent hydrogen and
$R^1$, $R^4$, $R^5$, X and Y have the abovementioned meanings, are reacted with orthocarboxylic acid esters of the formula (XXIV)

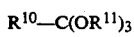

$$R^{10}-C(OR^{11})_3 \quad (XXIV)$$

in which $R^{10}$ and $R^{11}$ have the abovementioned meanings, if appropriate in the presence of a diluent, such as, for example, chloroform, toluene or chlorobenzene, and if appropriate in the presence of a catalyst, such as, for example, p-toluenesulphonic acid, at temperatures between 50° C. and 200° C.

The orthocarboxylic acid esters of the formula (XXIV) are known chemicals for organic synthesis.

In formula (XXV), $R^4$, $R^5$ and Y preferably or in particular have those meanings which have already been indicated above as preferred or as particularly preferred for $R^4$, $R^5$ and Y in the description of the compounds of the formula (I) according to the invention and $R^{10}$ and $R^{11}$ preferably represent $C_1-C_6$-alkyl, $C_2-C_6$-alkenyl, $C_2-C_6$-alkinyl, $C_3-C_6$-cycloalkyl, phenyl or benzyl; $R^{10}$ also represents hydrogen; $R^{10}$ in particular represents hydrogen, methyl, ethyl, propyl, phenyl or benzyl and $R^{11}$ represents methyl, ethyl, propyl or benzyl.

The hydride complexes of the formula (IX) further needed as starting substances in process (e) are known chemicals for synthesis.

Process (a) according to the invention is preferably carried out in the presence of a diluent.

Suitable diluents for carrying out process (a) according to the invention are in particular inert organic solvents. These include, for example, aliphatic, alicyclic or aromatic, optionally halogenated hydrocarbons, such as benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, nitriles, such as acetonitrile or propionitrile, amides, such as-dimethylformamide, dimethylacetamide, N-methylformanilide, N-methylpyrrolidone or hexamethylphosphoric triamide or esters, such as ethyl acetate.

Process (a) according to the invention is optionally carried out in the presence of a suitable reaction auxiliary. Those which are suitable are all customary inorganic or organic bases. These include, for example, tertiary amines, such as triethylamine, N,N-dimethylaniline, N,N-diethylbenzylamine, N,N-dimethylcyclohexylamine or dibutyltin dilaureate, pyridine, N,N-dimethylaminopyridine, diazabicyclooctane (DABCO), diazabicyclononene (DBN) or diazabicycloundecene (DBU).

When carrying out process (a) according to the invention, the reaction temperatures can be varied within a substantial range. In general, the reaction is carried out at temperatures between 0° C. and 150° C., preferably at temperatures between 10° C. and 100° C.

To carry out process (a) according to the invention, 1.0 to 2.0 mol, preferably 1.0 to 1.5 mol, of iso(thio)cyanate of the formula (III) and optionally 0.001 to 2.0 mol, preferably 0.001 to 1.0 mol, of reaction auxiliary are in general employed relative to 1 mol of 4,5-diamino-1,2,4-triazol-3-(thi)one of the formula (II). The reaction is carried out and the reaction products are worked up and isolated by generally customary methods.

Suitable acids for carrying out process (b) according to the invention are all inorganic and organic acids which can customarily be used for hydrazone cleavages. Inorganic mineral acids such as hydrochloric acid, sulphuric acid or phosphoric acid are preferably used.

Suitable diluents for carrying out process (b) according to the invention are all customary organic or inorganic solvents. Polar water-miscible organic solvents, in particular alcohols, such as methanol, ethanol, propanol or butanol, or their mixtures with water or pure water as a diluent are preferably used.

When carrying out process (b) according to the invention, the reaction temperatures can be varied within a substantial range. In general, the reaction is carried out at temperatures between 20° C. and 150° C., preferably at temperatures between 50° C. and 120° C.

Process (b) according to the invention is customarily carried out at normal pressure or under reduced pressure. If it is carried out under reduced pressure, suitable pressure ranges are between 20 and 400 mbar, preferably between 100 and 200 mbar.

To carry out process (b) according to the invention, 0.01 to 50 mol, preferably 0.1 to 20 mol, of an acid are in general employed relative to 1 mol of 4-alkylideneamino-5-amino-1,2,4-triazole-3-(thi)one of the formula (IV).

In general, the compound of the formula (IV) is dissolved in a suitable diluent, then the necessary amount of acid is added to it and the mixture is slowly concentrated under reduced pressure over the course of several hours.

In a particular embodiment, it is also possible to carry out process (b) according to the invention and the preparation of the precursors of the formula (IV) needed for this in one reaction step in a so-called one-pot process.

In this case there is the possibility of selecting the compounds of the formula (XXIII) as starting substances and reacting these successively in the one-pot process with amines of the formula (VI) and then with acid as in process (b) according to the invention or, alternatively, of selecting the compounds of the formula (XXI) as starting substances and reacting these successively in the one-pot process either with (thio)chloroformic acid esters of the formula (XXII), then with amines of the formula (VI), or with iso(thio)cyanates of the formula (III) and then with acid as in process (b) according to the invention.

Suitable diluents for carrying out process (c) according to the invention are inert organic solvents. These in particular include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide or esters, such as ethyl acetate, or sulphoxides, such as dimethyl sulphoxide.

Process (c) according to the invention can optionally be carried out in the presence of a suitable reaction auxiliary. Those which are suitable are all customary inorganic or organic bases. These include, for example, potassium hydroxide, alkali metal carbonates, such as sodium carbonate, potassium carbonate or sodium hydrogen carbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (c) according to the invention, the reaction temperatures can be varied within a substantial range. In general, the reaction is carried out at temperatures between 0° C. and 120° C., preferably at temperatures between 20° C. and 50° C.

To carry out process (c) according to the invention, 1 to 5 mol, preferably 1.0 to 2.5 mol, of amino compound of the formula (VI) and optionally 0.1 to 2 mol, preferably 1.0 to 1.2 mol, of reaction auxiliary are in general employed relative to 1 mol of substituted 1,2,4-triazol-3-(thi)one of the formula (V).

The reaction is carried out and the reaction products are worked up and isolated by generally customary methods.

In a particular embodiment, it is also possible to carry out process (c) according to the invention and the preparation of the precursors of the formula (V) needed for this in one reaction step in a so-called one-pot process.

Compounds of the formula (II) are used as starting materials in this case and these are reacted successively in the one-pot process, first with (thio)chloroformic acid esters of the formula (XXII) and then with amines of the formula (VI) as in process (c) according to the invention.

Process (d) according to the invention is preferably carried out in the presence of a diluent. The same solvents can be used in this process as are indicated above for process (a) according to the invention.

Process (d) is preferably carried out in the presence of a reaction auxiliary. The same reaction auxiliaries can be employed in this process as are indicated above for process (c) according to the invention.

In process (d) according to the invention, the reaction temperatures can be varied within a substantial range. In general, the reaction is carried out at temperatures between 0° C. and 150° C., preferably at temperatures between 10° C. and 120° C.

To carry out process (d) according to the invention, 1 to 2 mol, preferably 1.0 to 1.5 mol, of (thio)urethane of the formula (VII) are in general employed relative to 1 mol of 4,5-diamino-1,2,4-triazol-3-(thi)one of the formula (II).

The reaction is carried out and the products of the formula (I) are worked up and isolated by generally customary methods.

Process (e) according to the invention is preferably carried out in the presence of a polar solvent. Those which are suitable are preferably water, alcohols such as methanol, ethanol, propanol, isopropanol, butanol, isobutanol, sec-butanol and tert-butanol, ether alcohols such as methoxyethanol and ethoxyethanol, or ethers such as diethyl ether, dipropyl ether, diisopropyl ether, tetrahydrofuran and dioxane.

The reaction temperatures in the second step of process (e) can be varied within a substantial range. In general, the reaction is carried out at temperatures between −20° C. and +100° C., preferably between 0° C. and +30° C.

To carry out process (e) according to the invention, 0.5 to 5 mol, preferably 1 to 3 mol, of hydride complex of the formula (IX) are employed relative to 1 mol of 4-oxyalkylideneamino-5-amino-1,2,4-triazol-3-(thi)one of the formula (VIII).

The reaction is carried out and the reaction products are worked up and isolated by generally customary methods.

Process (f) according to the invention is carried out using a reducing agent and if appropriate a catalyst. Suitable systems of reducing agents and catalysts are, for example, hydrogen in combination with customary hydrogenation catalysts, such as, for example, Raney nickel, palladium or platinum, and also possibly complex metal hydrides, such as, for example, lithium aluminium hydride, sodium borohydride and sodium cyanoborohydride, if appropriate in combination with acidic catalysts, such as, for example, hydrochloric acid or acetic acid.

Process (f) is preferably carried out in the presence of a diluent. The same solvents can be used in this case as are indicated above for process (e) according to the invention.

The reaction temperatures in process (f) according to the invention can be varied within a substantial range. In general, the reaction is carried out at temperatures between −20° C. and +100° C., preferably at temperatures between 0° C. and +30° C.

The reaction is carried out and the reaction products are worked up and isolated by customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculss and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture land, and for the selective combating of weeds in annual cultures.

The compounds of the formula (I) according to the invention are suitable in particular for selectively combating monocotyledon and dicotyledon weeds in monocotyledon cultures, such as, for example, in maize, in particular in the post-emergence method.

The compounds of the formula (I) percolate extremely slowly into the soil; pollution of the ground water is thus virtually excluded.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaves on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound as well as very fine capsules in polymeric substances.

These formulations are produced in a known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H) (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beet and 4-amino-6-(1,1-dimethylethyl)-3-methylthio-1,2,4-triazin-5(4H)-one (METRIBUZIN) for combating weeds in soya beans; and also 2,4-dichlorophenoxyacetic acid (2,4-D); 4-(2,4-dichlorophenoxy)-butyric acid (2,4-DB); 2,4-dichlorophenoxypropionic acid (2,4-DP); 2-chloro-2',6'-diethyl-N-methoxy-methylacetanilide(ALACHLOR);2-chloro-4-ethylamino-6-isopropylamino-1,3,5-triazine (ATRAZINE); 3-isopropyl-2,1,3-benzothiadiazin-4-one-2,2-dioxide (BENTAZONE); 2-chloro-4-ethylamino-6-(3-cyanopropylamino)-1,3,5-triazine (CYANAZINE); 4-amino-6-t-butyl-3-ethylthio-1,2,4-triazin-5(4H)-one(E-THIOZIN); 3,5-diiodo-4-hydroxybenzonitrile (IOXYNIL); N-methyl-2-(1,3-benzothiazol-2-yloxy)-acetanilide (MEFENACET); 2-chloro-N-(2,6-dimethyl-phenyl)-N-[(1H)-pyrazol-1-yl-methyl]-acetamide (METAZACHLOR); 2-ethyl-6-methyl-N-(1-methyl-2-methoxyethyl)-chloroacetanilide (METOLACHLOR); O-(6-chloro-3-phenyl-pyridazin-4-yl) S-octyl thiocarbonate (PYRIDATE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON). Some mixtures surprisingly also exhibit a synergistic effect.

A mixture with other known active compounds, such as fungicides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5.0 kg per ha.

The preparation and the use of the active compounds according to the invention can be seen from the following examples.

PREPARATION EXAMPLES

EXAMPLE 1

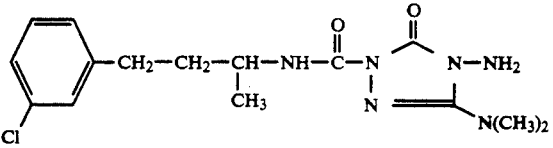

(Process (b)—with preparation of the precursor in the "one-pot process")

A mixture of 5.2 g (15 mmol) of 2-phenoxycarbonyl-4-(3-methyl-2-butylidene-amino)-5-dimethylamino-2,4-dihydro-3H-1,2,4-triazol-3-one, 3.36 g (18 mmol) of 1-methyl-3-(3-chloro-phenyl)-propylamine and 50 ml of tetrahydrofuran is stirred at 20° C. for 24 hours. It is then concentrated in a water-jet vacuum, the residue is taken up in 100 ml of ethanol and, after addition of 20 ml of water and 5 ml of conc. hydrochloric acid, the mixture is stirred at 60° C./200 mbar for 3 hours. After concentration in a water-jet vacuum, the residue is extracted with 150 ml of methylene chloride/150 ml of saturated sodium hydrogen carbonate solution in water, and the organic phase is separated off, dried using sodium sulphate and filtered. The filtrate is concentrated and the residue is further purified by column chromatography (silica gel and cyclohexane/ethyl acetate 1:3). The contents of the main fraction are crystallized by trituration with ether/petroleum ether and isolated by filtering with suction.

3.3 g (73% of theory) of 2-(1-methyl-3-(3-chloro-phenyl)-propyl-amino-carbonyl)-4-amino-5-dimethylamino-2,4-dihydro-3H-1,2,4-triazol-3-one of melting point 74° C. are obtained.

EXAMPLE 2

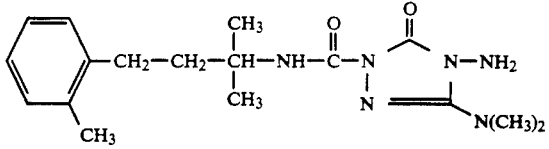

(Process (b)—with preparation of the precursor in the "one-pot process")

A mixture of 4.5 g (20 mmol) of 4-(3-methyl-2-butylideneamino)-5-dimethylamino-2,4-dihydro-3H-1,2,4-triazol-3-one, 4.1 g (20 mmol) of 1,1-dimethyl-3-(2-methyl-phenyl)-propyl isocyanate, 0.1 g of 1,8-diazabiy-clo-[5.4.0]-undec-7-ene and 100 ml of methylene chloride is stirred at 20° C. for 18 hours. It is then concentrated in a waterjet vacuum, the residue is taken up in 100 ml of ethanol and the mixture is stirred at 60° C./200 mbar for 3 hours after adding 20 ml of water and 5 ml of conc. hydrochloric acid. After concentration in a water-jet vacuum, the residue is extracted with 200 ml of methylene chloride/200 ml of saturated aqueous sodium hydrogen carbonate, and the organic phase is separated off, dried with magnesium sulphate and filtered. After concentration of the filtrate, the residue is crystallized by trituration with ether/petroleum ether and the crystalline product is isolated by filtering with suction.

4.5 g (65% of theory) of 2-(1,1-dimethyl-3-(2-methylphenyl)-propyl-amino-carbonyl)-4-amino-5-dimethylamino-2,4-dihydro-3H-1,2,4-triazol-3-one of melting point 117° C. are obtained.

The compounds of the formula (I)

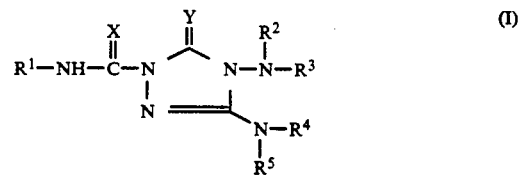

(I)

shown in Table 1 below can also be prepared, for example, analogously to Examples 1 and 2 and in accordance with the general description of the preparation processes according to the invention.

TABLE 1
Examples of the compounds of the formula (I)

| Ex. No. | $R^1$ | $R^2$ | $R^3$ | $R^4$ | $R^5$ | X | Y | Melting point (°C.) |
|---|---|---|---|---|---|---|---|---|
| 3 | phenyl-CH₂-CH₂-C(CH₃)₂- | H | H | CH₃ | CH(CH₃)₂ | O | O | (amorphous) |
| 4 | phenyl-CH₂-CH₂-CH₂- | H | H | CH₃ | CH₃ | O | O | 109 |
| 5 | 3-(F₃C)-phenyl-CH₂-CH₂-CH(CH₃)- | H | H | CH₃ | CH₃ | O | O | 114 |
| 6 | 4-(H₃C)-phenyl-CH₂-CH₂-CH(CH₃)- | H | H | CH₃ | CH₃ | O | O | 109 |
| 7 | 3-(H₃C)-phenyl-CH₂-CH₂-CH(CH₃)- | H | H | CH₃ | CH₃ | O | O | (amorphous) |
| 8 | 2,4-Cl₂-phenyl-CH₂-CH₂-CH(CH₃)- | H | H | CH₃ | CH₃ | O | O | (amorphous) |
| 9 | 4-F-phenyl-CH₂-CH₂-CH(CH₃)- | H | H | CH₃ | CH₃ | O | O | (amorphous) |
| 10 | 4-Cl-phenyl-CH₂-CH₂-CH(CH₃)- | H | H | CH₃ | CH₃ | O | O | 97 |
| 11 | 2-Cl-phenyl-CH₂-CH₂-CH(CH₃)- | H | H | CH₃ | CH₃ | O | O | 110 |

| | | | | | | | | |
|---|---|---|---|---|---|---|---|---|
| 12 | 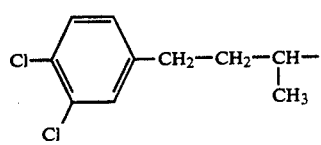 | H | H | CH$_3$ | CH$_3$ | O | O | (amorphous) |
| 13 | 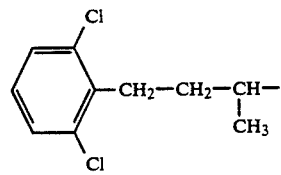 | H | H | CH$_3$ | CH$_3$ | O | O | 56 |
| 14 | 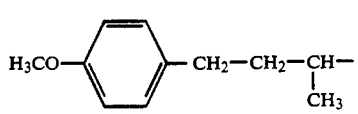 | H | H | CH$_3$ | CH$_3$ | O | O | (amorphous) |
| 15 | 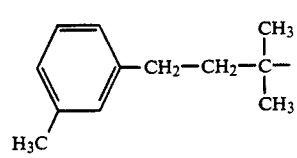 | H | H | CH$_3$ | CH$_3$ | O | O | 131 |
| 16 | 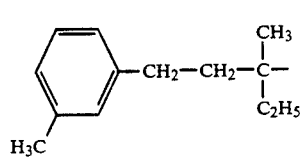 | H | H | CH$_3$ | CH$_3$ | O | O | (amorphous) |
| 17 | 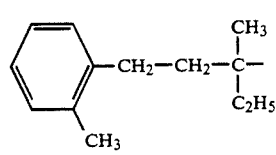 | H | H | CH$_3$ | CH$_3$ | O | O | 93 |
| 18 | 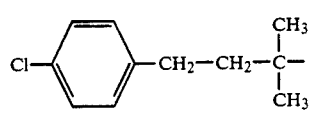 | H | H | CH$_3$ | CH$_3$ | O | O | 137 |
| 19 | 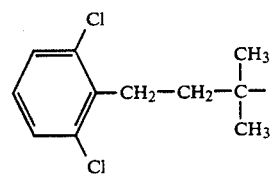 | H | H | CH$_3$ | CH$_3$ | O | O | 158 |
| 20 | 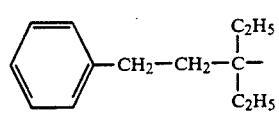 | H | H | CH$_3$ | CH$_3$ | O | O | 97 |
| 21 | 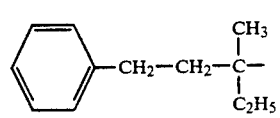 | H | H | CH$_3$ | CH$_3$ | O | O | (amorphous) |
| 22 | 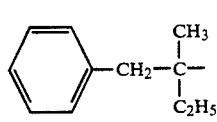 | H | H | CH$_3$ | CH$_3$ | O | O | 111 |

-continued

| # | Structure | | | | | | |
|---|---|---|---|---|---|---|---|
| 23 | H₃C–C₆H₄–CH₂–CH₂–C(CH₃)₂–CH₃ | H | H | CH₃ | CH₃ | O | O | 106 |
| 24 | H₃C–C₆H₄–CH₂–C(CH₃)₂–CH(CH₃)–CH₃ | H | H | CH₃ | CH₃ | O | O | 154 |
| 25 | H₃C–C₆H₄–CH₂–C(CH₃)₂–C(CH₃)₂–CH₃ | H | H | CH₃ | CH₃ | O | O | 168 |
| 26 | 3-Cl–C₆H₄–CH₂–CH₂–C(CH₃)₂–CH₃ | H | H | CH₃ | CH₃ | O | O | 118 |
| 27 | 2,4-Cl₂–C₆H₃–CH₂–CH₂–C(CH₃)₂–CH₃ | H | H | CH₃ | CH₃ | O | O | 108 |
| 28 | 2,4-Cl₂–C₆H₃–CH₂–CH₂–CH(CH₃)–CH₃ | H | H | CH₃ | CH₃ | O | O | 125 |
| 29 | C₆H₅–CH₂–C(CH₃)(CH₂CH(CH₃)₂)– | H | H | CH₃ | CH₃ | O | O | (amorphous) |
| 30 | 4-F–C₆H₄–CH₂–CH₂–C(CH₃)₂–CH₃ | H | H | CH₃ | CH₃ | O | O | 112 |
| 31 | 3-Cl–C₆H₄–O–CH₂–C(CH₃)₂–CH(CH₃)–CH₃ | H | H | CH₃ | CH₃ | O | O | (amorphous) |
| 32 | 4-Cl–C₆H₄–CH(C₂H₅)– | H | H | CH₃ | CH₃ | O | O | (amorphous) |
| 33 | 3-methylcyclohexyl | H | H | CH₃ | CH₃ | O | O | (amorphous) |
| 34 | 4-methylcyclohexyl | H | H | CH₃ | CH₃ | O | O | (amorphous) |

-continued
| | | | | | | | |
|---|---|---|---|---|---|---|---|
| 35 | 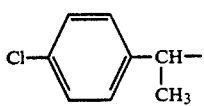 | H | H | CH$_3$ | CH$_3$ | O | O | (amorphous) |
| 36 | 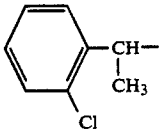 | H | H | CH$_3$ | CH$_3$ | O | O | 106 |
| 37 | 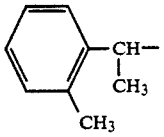 | H | H | CH$_3$ | CH$_3$ | O | O | (amorphous) |
| 38 | 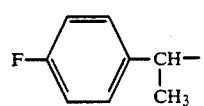 | H | H | CH$_3$ | CH$_3$ | O | O | (amorphous) |
| 39 | 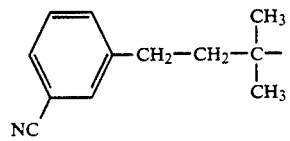 | H | H | CH$_3$ | CH$_3$ | O | O | 113 |
| 40 | 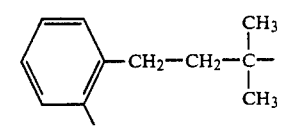 | H | H | CH$_3$ | CH$_3$ | O | O | 121 |
| 41 | 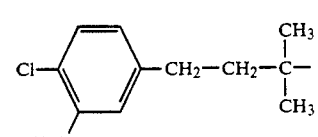 | H | H | CH$_3$ | CH$_3$ | O | O | 118 |
| 42 | 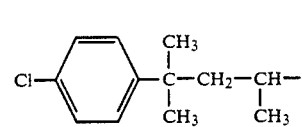 | H | H | CH$_3$ | CH$_3$ | O | O | 103 |
| 43 | 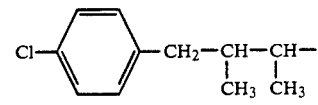 | H | H | CH$_3$ | CH$_3$ | O | O | 162 |
| 44 | 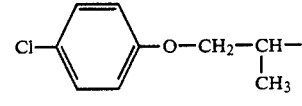 | H | H | CH$_3$ | CH$_3$ | O | O | 55 |
| 45 | 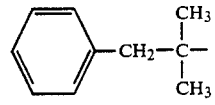 | H | CH$_3$ | H | CH$_3$ | O | O | 148 |
| 46 | 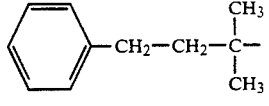 | H | CH$_3$ | H | CH$_3$ | O | O | 110 |

-continued

| # | R | | | | | | | |
|---|---|---|---|---|---|---|---|---|
| 47 | PhCH₂-CH(CH₃)- | H | CH₃ | H | CH₃ | O | O | 167 |
| 48 | (CH₃)₂CH—CH₂— | H | CH₃ | H | CH₃ | O | O | 127 |
| 49 | 4-Cl-C₆H₄-C(CH₃)₂-CH₂- | H | CH₃ | H | CH₃ | O | O | 119 |
| 50 | CH₃—CH₂—CH₂—CH(CH₃)— | H | CH₃ | H | CH₃ | O | O | 119 |
| 51 | 4-(CH₃)₃C-cyclohexyl- | H | CH₃ | H | CH₃ | O | O | 119 |
| 52 | 4-Br-C₆H₄-CH(CH₃)- | H | CH₃ | H | CH₃ | O | O | 126 |
| 53 | 3,4-Cl₂-C₆H₃-CH(CH₃)- | H | CH₃ | H | CH₃ | O | O | 158 |
| 54 | 4-C₂H₅-C₆H₄-CH(CH₃)- | H | CH₃ | H | CH₃ | O | O | 113 |
| 55 | 2,4-Cl₂-C₆H₃-CH(CH₃)- | H | CH₃ | H | CH₃ | O | O | 165 |
| 56 | 4-F-C₆H₄-CH(CH₃)- | H | CH₃ | H | CH₃ | O | O | 124 |
| 57 | 4-CH₃-C₆H₄-CH(CH₃)- | H | CH₃ | H | CH₃ | O | O | 97 |
| 58 | 4-CH₃O-C₆H₄-CH(CH₃)- | H | CH₃ | H | CH₃ | O | O | 96 |
| 59 | 3-Br-C₆H₄-CH(CH₃)- | H | CH₃ | H | CH₃ | O | O | 134 |

| | | | | | | | | |
|---|---|---|---|---|---|---|---|---|
| 60 | 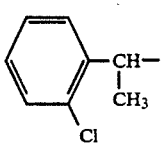 | H | CH$_3$ | H | CH$_3$ | O | O | 160 |
| 61 | 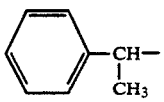 | H | CH$_3$ | H | CH$_3$ | O | O | 51 |
| 62 | 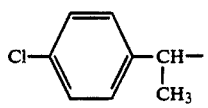 | H | CH$_3$ | H | CH$_3$ | O | O | 122 |
| 63 | 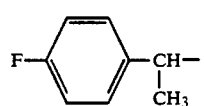 | H | CH$_3$ | H | CH$_3$ | O | O | (amorphous) |
| 64 | 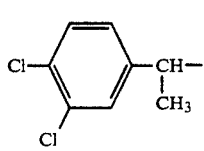 | H | CH$_3$ | H | CH$_3$ | S | O | 164 |
| 65 | 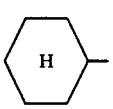 | H | CH$_3$ | H | CH$_3$ | S | O | 127 |
| 66 | 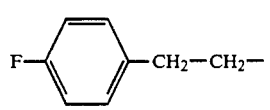 | H | CH$_3$ | H | CH$_3$ | S | O | 111 |
| 67 | 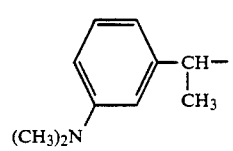 | H | CH$_3$ | H | CH$_3$ | O | O | 135 |
| 68 | 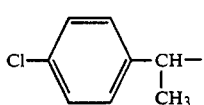 | H | CH$_3$ | H | CH$_3$ | O | O | 102 |
| 69 | 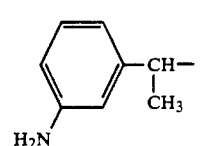 | H | CH$_3$ | H | CH$_3$ | O | O | 119 |
| 70 | 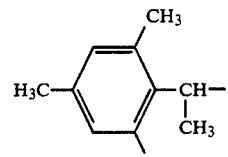 | H | CH$_3$ | H | CH$_3$ | O | O | 197 |
| 71 | 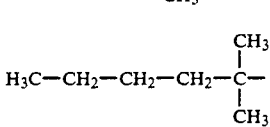 | H | H | CH$_3$ | CH$_3$ | O | O | 79 |

-continued

| № | R | | | | | X | Y | mp/n |
|---|---|---|---|---|---|---|---|---|
| 72 | C₆H₅-CH₂-CH₂-C(CH₃)₂-CH₃ | H | H | H | CH₃ | O | O | 128 |
| 73 | C₆H₅-CH₂-CH₂-C(CH₃)₂-CH₃ | H | CH₃ | CH₃ | CH₃ | O | O | 103 |
| 74 | C₆H₅-CH₂-C(CH₃)₂-CH₃ | H | CH₃ | CH₃ | CH₃ | O | O | 158 |
| 75 | C₆H₅-CH₂-CH₂-C(CH₃)₂-CH₃ | CH₃ | CH₃ | H | CH₃ | O | O | 108 |
| 76 | 4-(CH₃)₃C-C₆H₁₀- | H | H | CH₃ | CH₃ | O | O | (amorphous) |
| 77 | CH₃-CH₂-CH₂-CH(CH₃)- | H | H | CH₃ | CH₃ | O | O | (amorphous) |
| 78 | C₆H₅-CH₂-CH(CH₃)- | H | H | CH₃ | CH₃ | O | O | (amorphous) |
| 79 | C₆H₅-CH₂-CH₂-CH(CH₃)- | H | H | CH₃ | CH₃ | O | O | $n_D^{20} = 1.5482$ |
| 80 | C₆H₅-CH₂-CH₂-CH(C₄H₉)- | H | H | CH₃ | CH₃ | O | O | $n_D^{20} = 1.5244$ |
| 81 | C₆H₅-CH₂-CH₂-CH₂-C(CH₃)₂-CH₃ | H | H | CH₃ | CH₃ | O | O | 120 |
| 82 | 4-H₃CO-C₆H₄-CH₂-CH₂-C(CH₃)₂-CH₃ | H | H | CH₃ | CH₃ | O | O | $n_D^{20} = 1.5321$ |
| 83 | C₆H₅-CH(CH₃)- | H | H | CH₃ | CH₃ | S | O | (amorphous) |
| 84 | CH₃-CH₂-C(CH₃)₂-CH₃ | H | H | CH₃ | CH₃ | S | O | 126 |
| 85 | CH₃-CH₂-CH(CH₃)- | H | H | CH₃ | CH₃ | S | O | 94 |

| | | | | | | | |
|---|---|---|---|---|---|---|---|
| 86 | 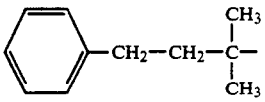 | H | H | CH₃ | CH₃ | S | O | 122 |
| 87 | 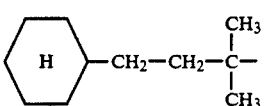 | H | H | CH₃ | CH₃ | O | O | 100 |
| 88 | 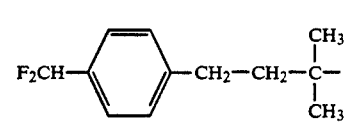 | H | H | CH₃ | CH₃ | O | O | 87 |
| 89 | 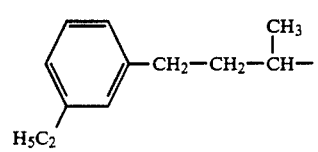 | H | H | CH₃ | CH₃ | O | O | |
| 90 | 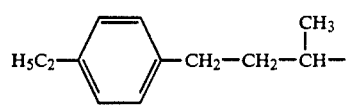 | H | H | CH₃ | CH₃ | O | O | |
| 91 | 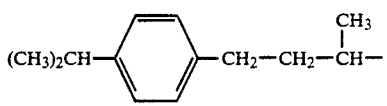 | H | H | CH₃ | CH₃ | O | O | |
| 92 | 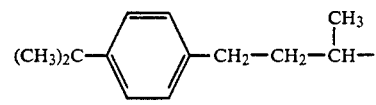 | H | H | CH₃ | CH₃ | O | O | |
| 93 | 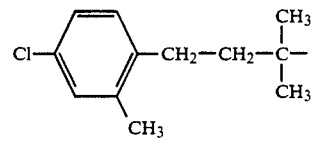 | H | H | CH₃ | CH₃ | O | O | |
| 94 | 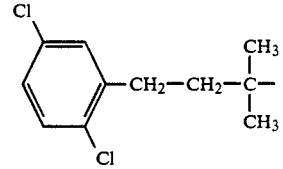 | H | H | CH₃ | CH₃ | O | O | |
| 95 | 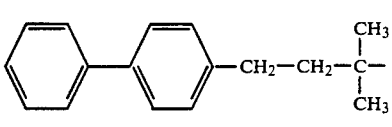 | H | H | CH₃ | CH₃ | O | O | |
| 96 | 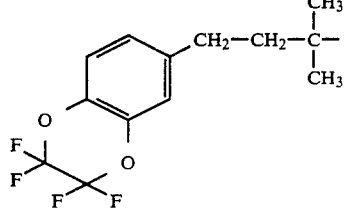 | H | H | CH₃ | CH₃ | O | O | |

-continued

| # | Structure | | | | | | | |
|---|---|---|---|---|---|---|---|---|
| 97 | NC-C6H4-CH2-C(CH3)3 | H | H | CH3 | CH3 | O | O | |
| 98 | H5C2OOC-C6H4-CH2-C(CH3)3 | H | H | CH3 | CH3 | O | O | |
| 99 | 3-(COOC2H5)-C6H4-CH2-CH2-C(CH3)3 | H | H | CH3 | CH3 | O | O | |
| 100 | n-C3H7OOC-C6H4-CH2-CH2-C(CH3)3 | H | H | CH3 | CH3 | O | O | |
| 101 | 3-(COO-n-C3H7)-C6H4-CH2-CH2-C(CH3)3 | H | H | CH3 | CH3 | O | O | |
| 102 | 2-CH3-C6H4-CH2-C(CH3)3 | H | H | CH3 | CH3 | O | O | |
| 103 | (CH3)3C-C6H4-CH2- | H | H | CH3 | CH3 | O | O | |
| 104 | H5C2-C6H4-CH(CH3)- | H | H | CH3 | CH3 | O | O | |
| 105 | Cl-C6H4-CH2-C(CH3)3 | H | H | CH3 | CH3 | O | O | 115 |
| 106 | Cl-C6H4-CH2-CH(CH3)2 | H | H | CH3 | CH3 | O | O | |
| 107 | F3C-C6H4-CH2-CH2-C(CH3)3 | H | H | CH3 | CH3 | O | O | 114 |
| 108 | 3,4-F2-C6H3-CH2-CH2-C(CH3)3 | H | H | CH3 | CH3 | O | O | 128 |

-continued

| | | | | | | | |
|---|---|---|---|---|---|---|---|
| 109 | H₃C—S—⟨phenyl⟩—CH₂—CH₂—C(CH₃)₂—CH₃ | H | H | CH₃ | CH₃ | O | O |
| 110 | F₂CH—O—⟨phenyl⟩—CH₂—CH₂—C(CH₃)₂—CH₃ | H | H | CH₃ | CH₃ | O | O |
| 111 | ⟨phenyl⟩—CH₂—CH₂—C(CH₃)(cyclohexyl) | H | H | CH₃ | CH₃ | O | O |
| 112 | Cl—⟨phenyl⟩—CH₂—CH₂—C(CH₃)(cyclohexyl) | H | H | CH₃ | CH₃ | O | O |
| 113 | ⟨phenyl⟩—C≡C—C(CH₃)(cyclohexyl) | H | H | CH₃ | CH₃ | O | O |
| 114 | Cl—⟨phenyl⟩—C≡C—C(CH₃)(cyclohexyl) | H | H | CH₃ | CH₃ | O | O |
| 115 | ⟨phenyl⟩—⟨cyclohexyl⟩— | H | H | CH₃ | CH₃ | O | O | 65 |
| 116 | Cl—⟨phenyl⟩—⟨cyclohexyl⟩— | H | H | CH₃ | CH₃ | O | O |
| 117 | ⟨phenyl⟩—CH₂—CH₂—C(CH₃)(cyclopropyl) | H | H | CH₃ | CH₃ | O | O |
| 118 | Cl—⟨phenyl⟩—CH₂—CH₂—C(CH₃)(cyclopropyl) | H | H | CH₃ | CH₃ | O | O |
| 119 | ⟨phenyl⟩—C≡C—C(CH₃)₂—CH₃ | H | H | CH₃ | CH₃ | O | O | 181 |

| | | | | | | | |
|---|---|---|---|---|---|---|---|
| 120 | 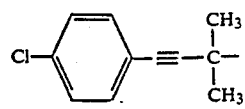 | H | H | CH₃ | CH₃ | O | O | 124 |
| 121 | 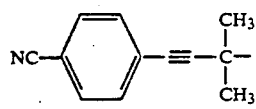 | H | H | CH₃ | CH₃ | O | O |
| 122 | 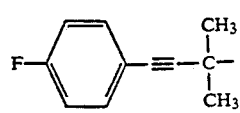 | H | H | CH₃ | CH₃ | O | O |
| 123 | 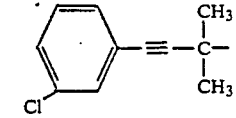 | H | H | CH₃ | CH₃ | O | O |
| 124 | 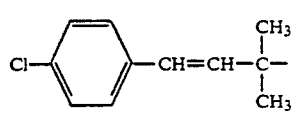 | H | H | CH₃ | CH₃ | O | O |
| 125 | 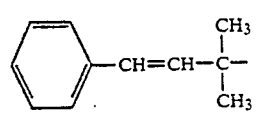 | H | H | CH₃ | CH₃ | O | O |
| 126 | 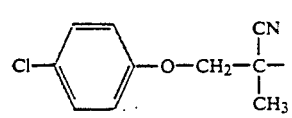 | H | H | CH₃ | CH₃ | O | O |
| 127 | 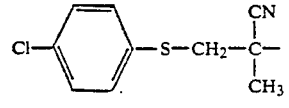 | H | H | CH₃ | CH₃ | O | O |
| 128 | 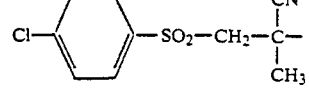 | H | H | CH₃ | CH₃ | O | O |
| 129 | 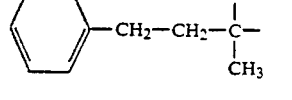 | H | H | CH₃ | CH₃ | O | O |
| 130 | 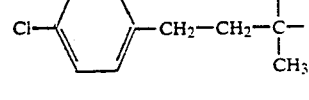 | H | H | CH₃ | CH₃ | O | O |
| 131 | 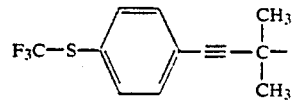 | H | H | CH₃ | CH₃ | O | O |
| 132 | 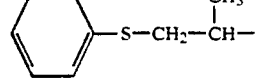 | H | H | CH₃ | CH₃ | O | O |

| # | Structure | | | | | |
|---|---|---|---|---|---|---|
| 133 | 4-Cl-C6H4-S-CH2-CH(CH3)- | H | H | CH3 | CH3 | O | O |
| 134 | C6H5-S-CH2-C(CH3)2-CH3 | H | H | CH3 | CH3 | O | O |
| 135 | 4-Cl-C6H4-S-CH2-C(CH3)2-CH3 | H | H | CH3 | CH3 | O | O | 130 |
| 136 | 4-(CH3)3C-C6H4-S-C(CH3)2-CH(CH3)- | H | H | CH3 | CH3 | O | O |
| 137 | 4-CH3-C6H4-O-CH2-CH(CH3)- | H | H | CH3 | CH3 | O | O |
| 138 | 4-CH3O-C6H4-O-CH2-CH(CH3)- | H | H | CH3 | CH3 | O | O |
| 139 | 4-Cl-3-CH3-C6H3-O-CH2-CH(CH3)- | H | H | CH3 | CH3 | O | O |
| 140 | 3,4-(CH3)2-C6H3-O-CH2-CH(CH3)- | H | H | CH3 | CH3 | O | O |
| 141 | 3-CH3-C6H4-O-CH2-CH(CH3)- | H | H | CH3 | CH3 | O | O |
| 142 | 3-Cl-C6H4-O-CH2-CH(CH3)- | H | H | CH3 | CH3 | O | O |
| 143 | 2,5-(CH3)2-C6H3-O-CH2-CH(CH3)- | H | H | CH3 | CH3 | O | O |

-continued

| # | Structure | | | | | | |
|---|---|---|---|---|---|---|---|
| 144 | 3,5-dimethyl-(isopropyl)-C₆H₃-O-CH₂-CH(CH₃)- | H | H | CH₃ | CH₃ | O | O |
| 145 | 2,6-dimethylphenyl-O-CH₂-CH(CH₃)- | H | H | CH₃ | CH₃ | O | O |
| 146 | 2,2-dimethylchroman-6-yl-O-CH₂-CH(CH₃)- | H | H | CH₃ | CH₃ | O | O |
| 147 | 2,2-dimethylchroman-8-yl-O-CH₂-CH(CH₃)- | H | H | CH₃ | CH₃ | O | O |
| 148 | C₆H₅-NH-CH₂-CH₂- | H | H | CH₃ | CH₃ | O | O |
| 149 | C₆H₅-N(CH₃)-CH₂-CH₂- | H | H | CH₃ | CH₃ | O | O |
| 150 | C₆H₅-N(C₂H₅)-CH₂-CH₂- | H | H | CH₃ | CH₃ | O | O |
| 151 | C₆H₅-N(COC₂H₅)-CH₂-CH₂- | H | H | CH₃ | CH₃ | O | O |
| 152 | 3-CH₃O-C₆H₄-CH₂-CH(CH₃)-CH(CH₃)- | H | H | CH₃ | CH₃ | O | O |
| 153 | 3-C₂H₅O-C₆H₄-CH₂-CH(CH₃)-CH(CH₃)- | H | H | CH₃ | CH₃ | O | O |
| 154 | 3-n-C₃H₇O-C₆H₄-CH₂-CH(CH₃)-CH(CH₃)- | H | H | CH₃ | CH₃ | O | O |

| | | | | | | |
|---|---|---|---|---|---|---|
| 155 | 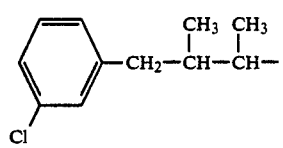 | H | H | $CH_3$ | $CH_3$ | O | O |
| 156 | 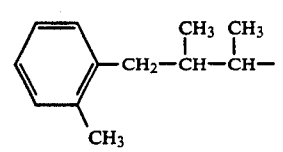 | H | H | $CH_3$ | $CH_3$ | O | O |
| 157 | 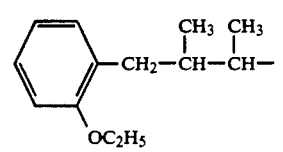 | H | H | $CH_3$ | $CH_3$ | O | O |
| 158 | 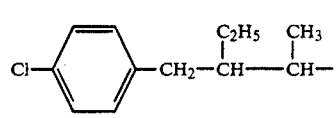 | H | H | $CH_3$ | $CH_3$ | O | O |
| 159 | 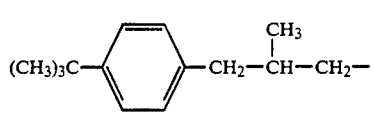 | H | H | $CH_3$ | $CH_3$ | O | O |
| 160 | 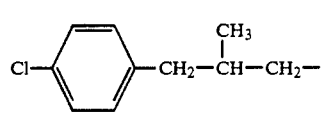 | H | H | $CH_3$ | $CH_3$ | O | O |
| 161 | 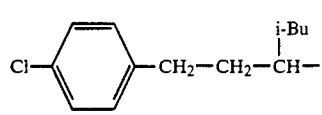 | H | H | $CH_3$ | $CH_3$ | O | O |
| 162 | 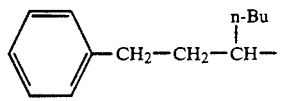 | H | H | $CH_3$ | $CH_3$ | O | O |
| 163 | 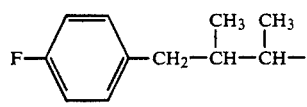 | H | H | $CH_3$ | $CH_3$ | O | O |
| 164 | 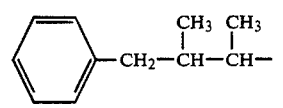 | H | H | $CH_3$ | $CH_3$ | O | O |
| 165 | 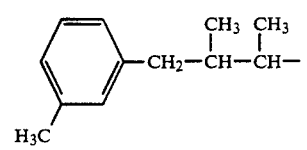 | H | H | $CH_3$ | $CH_3$ | O | O |
| 166 | 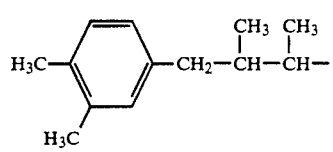 | H | H | $CH_3$ | $CH_3$ | O | O |

-continued
| | | | | | | | |
|---|---|---|---|---|---|---|---|
| 167 | 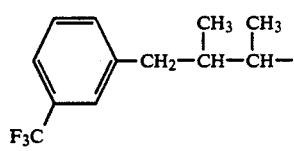 | H | H | CH₃ | CH₃ | O | O |
| 168 | 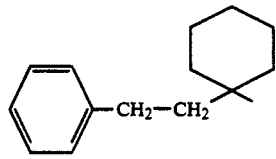 | H | CH₃ | H | CH₃ | O | O |
| 169 | 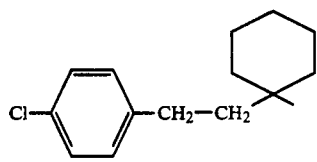 | H | CH₃ | H | CH₃ | O | O |
| 170 | 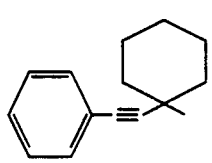 | H | CH₃ | H | CH₃ | O | O |
| 171 | 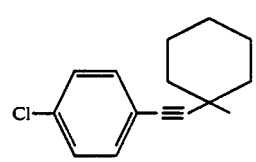 | H | CH₃ | H | CH₃ | O | O |
| 172 | 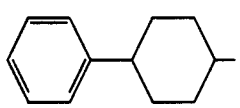 | H | CH₃ | H | CH₃ | O | O |
| 173 | 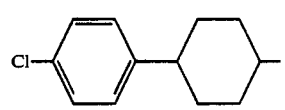 | H | CH₃ | H | CH₃ | O | O |
| 174 | 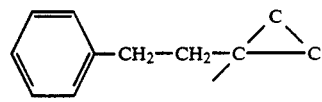 | H | CH₃ | H | CH₃ | O | O |
| 175 | 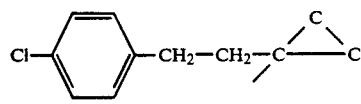 | H | CH₃ | H | CH₃ | O | O |
| 176 | 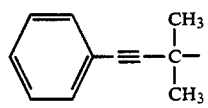 | H | CH₃ | H | CH₃ | O | O |
| 177 | 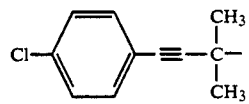 | H | CH₃ | H | CH₃ | O | O |

-continued

| No. | Structure | | | | | | |
|---|---|---|---|---|---|---|---|
| 178 | NC-C₆H₄-C≡C-C(CH₃)₂- | H | CH₃ | H | CH₃ | O | O |
| 179 | F-C₆H₄-C≡C-C(CH₃)₂- | H | CH₃ | H | CH₃ | O | O |
| 180 | 3-Cl-C₆H₄-C≡C-C(CH₃)₂- | H | CH₃ | H | CH₃ | O | O |
| 181 | 4-Cl-C₆H₄-CH=CH-C(CH₃)₂- | H | CH₃ | H | CH₃ | O | O |
| 182 | C₆H₅-CH=CH-C(CH₃)₂- | H | CH₃ | H | CH₃ | O | O |
| 183 | 4-Cl-C₆H₄-O-CH₂-C(CN)(CH₃)- | H | CH₃ | H | CH₃ | O | O |
| 184 | 4-Cl-C₆H₄-S-CH₂-C(CN)(CH₃)- | H | CH₃ | H | CH₃ | O | O |
| 185 | 4-Cl-C₆H₄-SO₂-CH₂-C(CN)(CH₃)- | H | CH₃ | H | CH₃ | O | O |
| 186 | C₆H₅-CH₂-CH₂-C(CN)(CH₃)- | H | CH₃ | H | CH₃ | O | O |
| 187 | 4-Cl-C₆H₄-CH₂-CH₂-C(CN)(CH₃)- | H | CH₃ | H | CH₃ | O | O |
| 188 | C₆H₅-S-CH₂-CH(CH₃)- | H | CH₃ | H | CH₃ | O | O |
| 189 | 4-Cl-C₆H₄-S-CH₂-CH(CH₃)- | H | CH₃ | H | CH₃ | O | O |
| 190 | C₆H₅-S-CH₂-C(CH₃)₂- | H | CH₃ | H | CH₃ | O | O |

-continued
| | | | | | | | |
|---|---|---|---|---|---|---|---|
| 191 | 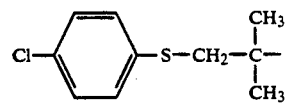 | H | CH₃ | H | CH₃ | O | O |
| 192 | 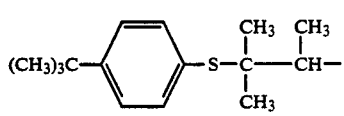 | H | CH₃ | H | CH₃ | O | O |
| 193 | 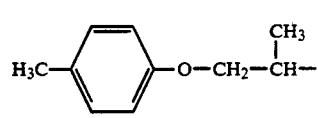 | H | CH₃ | H | CH₃ | O | O |
| 194 | 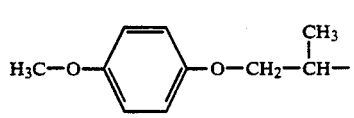 | H | CH₃ | H | CH₃ | O | O |
| 195 | 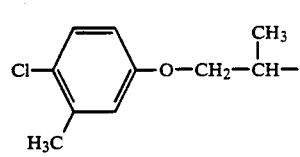 | H | CH₃ | H | CH₃ | O | O |
| 196 | 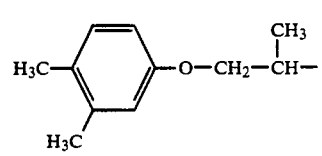 | H | CH₃ | H | CH₃ | O | O |
| 197 | 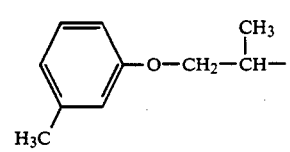 | H | CH₃ | H | CH₃ | O | O |
| 198 | 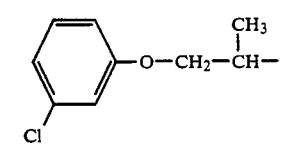 | H | CH₃ | H | CH₃ | O | O |
| 199 | 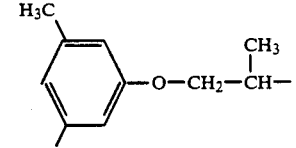 | H | CH₃ | H | CH₃ | O | O |
| 200 | 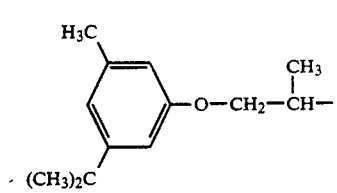 | H | CH₃ | H | CH₃ | O | O |
| 201 | 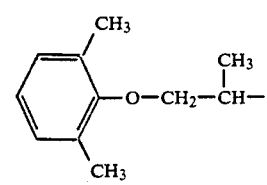 | H | CH₃ | H | CH₃ | O | O |

-continued

| # | Structure | | | | | | |
|---|---|---|---|---|---|---|---|
| 202 | 6-(isobutoxy)-2,2-dimethylchroman | H | CH₃ | H | CH₃ | O | O |
| 203 | 8-(isobutoxy)-2,2-dimethylchroman | H | CH₃ | H | CH₃ | O | O |
| 204 | C₆H₅-NH-CH₂-CH₂- | H | CH₃ | H | CH₃ | O | O |
| 205 | C₆H₅-N(CH₃)-CH₂-CH₂- | H | CH₃ | H | CH₃ | O | O |
| 206 | C₆H₅-N(C₂H₅)-CH₂-CH₂- | H | CH₃ | H | CH₃ | O | O |
| 207 | C₆H₅-N(COC₂H₅)-CH₂-CH₂- | H | CH₃ | H | CH₃ | O | O |
| 208 | 3-CH₃O-C₆H₄-CH₂-CH(CH₃)-CH(CH₃)- | H | CH₃ | H | CH₃ | O | O |
| 209 | 3-C₂H₅O-C₆H₄-CH₂-CH(CH₃)-CH(CH₃)- | H | CH₃ | H | CH₃ | O | O |
| 210 | 3-(n-C₃H₇O)-C₆H₄-CH₂-CH(CH₃)-CH(CH₃)- | H | CH₃ | H | CH₃ | O | O |
| 211 | 3-Cl-C₆H₄-CH₂-CH(CH₃)-CH(CH₃)- | H | CH₃ | H | CH₃ | O | O |
| 212 | 2-CH₃-C₆H₄-CH₂-CH(CH₃)-CH(CH₃)- | H | CH₃ | H | CH₃ | O | O |

-continued
| | | | | | | | |
|---|---|---|---|---|---|---|---|
| 213 | 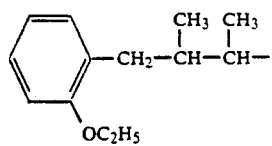 | H | CH₃ | H | CH₃ | O | O |
| 214 | 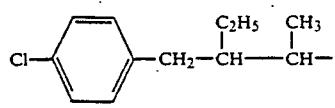 | H | CH₃ | H | CH₃ | O | O |
| 215 | 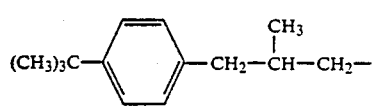 | H | CH₃ | H | CH₃ | O | O |
| 216 | 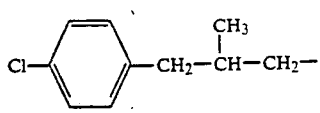 | H | CH₃ | H | CH₃ | O | O |
| 217 | 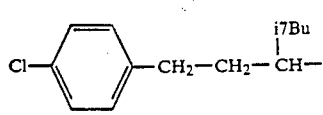 | H | CH₃ | H | CH₃ | O | O |
| 218 | 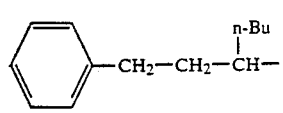 | H | CH₃ | H | CH₃ | O | O |
| 219 | 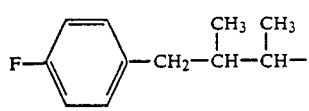 | H | CH₃ | H | CH₃ | O | O |
| 220 | 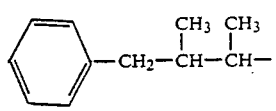 | H | CH₃ | H | CH₃ | O | O |
| 221 | 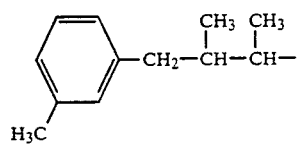 | H | CH₃ | H | CH₃ | O | O |
| 222 | 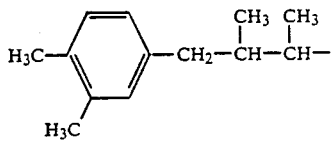 | H | CH₃ | H | CH₃ | O | O |
| 223 | 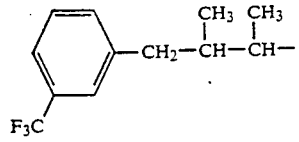 | H | CH₃ | H | CH₃ | O | O |
| 224 | 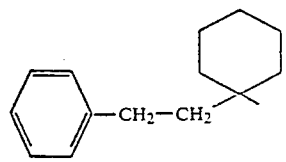 | H | CH₃ | CH₃ | CH₃ | O | O |

-continued
| | | | | | | | |
|---|---|---|---|---|---|---|---|
| 225 | 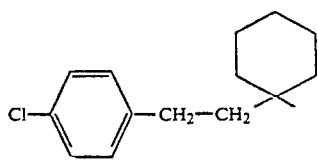 | H | CH₃ | CH₃ | CH₃ | O | O |
| 226 | 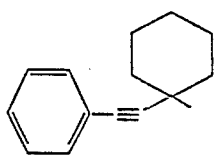 | H | CH₃ | CH₃ | CH₃ | O | O |
| 227 | 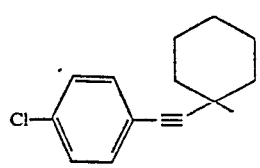 | H | CH₃ | CH₃ | CH₃ | O | O |
| 228 | 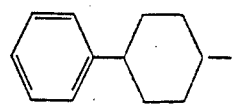 | H | CH₃ | CH₃ | CH₃ | O | O |
| 229 | 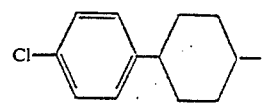 | H | CH₃ | CH₃ | CH₃ | O | O |
| 230 | 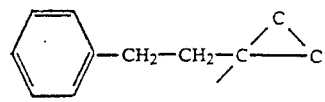 | H | CH₃ | CH₃ | CH₃ | O | O |
| 231 | 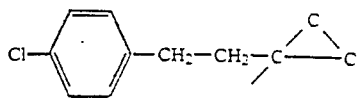 | H | CH₃ | CH₃ | CH₃ | O | O |
| 232 | 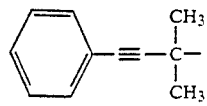 | H | CH₃ | CH₃ | CH₃ | O | O |
| 233 | 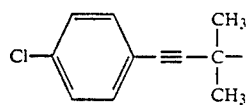 | H | CH₃ | CH₃ | CH₃ | O | O |
| 234 | 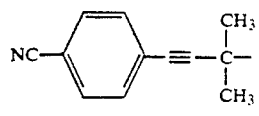 | H | CH₃ | CH₃ | CH₃ | O | O |
| 235 | 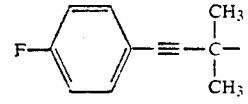 | H | CH₃ | CH₃ | CH₃ | O | O |
| 236 | 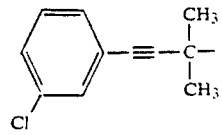 | H | CH₃ | CH₃ | CH₃ | O | O |
Note: For 225, 230 the substituent R (first after number) is shown as H with a period in the image for 230.

| | | | | | | | |
|---|---|---|---|---|---|---|---|
| 237 | 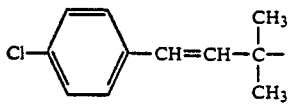 | H | CH₃ | CH₃ | CH₃ | O | O |
| 238 | 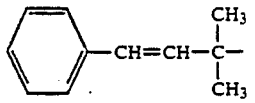 | H | CH₃ | CH₃ | CH₃ | O | O |
| 239 | 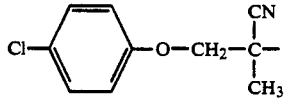 | H | CH₃ | CH₃ | CH₃ | O | O |
| 240 | 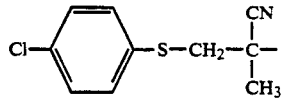 | H | CH₃ | CH₃ | CH₃ | O | O |
| 241 | 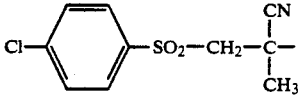 | H | CH₃ | CH₃ | CH₃ | O | O |
| 242 | 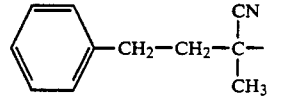 | H | CH₃ | CH₃ | CH₃ | O | O |
| 243 | 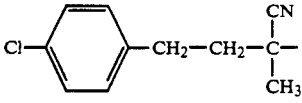 | H | CH₃ | CH₃ | CH₃ | O | O |
| 244 | 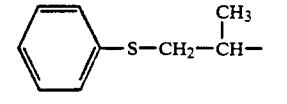 | H | CH₃ | CH₃ | CH₃ | O | O |
| 245 | 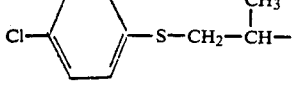 | H | CH₃ | CH₃ | CH₃ | O | O |
| 246 | 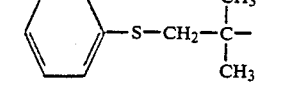 | H | CH₃ | CH₃ | CH₃ | O | O |
| 247 | 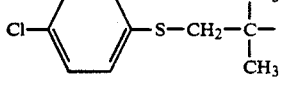 | H | CH₃ | CH₃ | CH₃ | O | O |
| 248 | 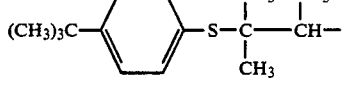 | H | CH₃ | CH₃ | CH₃ | O | O |
| 249 | 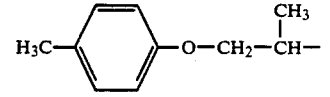 | H | CH₃ | CH₃ | CH₃ | O | O |

-continued

| No. | Structure | | | | | | |
|---|---|---|---|---|---|---|---|
| 250 | H3CO-C6H3-O-CH2-CH(CH3)- | H | CH3 | CH3 | CH3 | O | O |
| 251 | Cl,H3C-C6H3-O-CH2-CH(CH3)- | H | CH3 | CH3 | CH3 | O | O |
| 252 | (H3C)2-C6H3-O-CH2-CH(CH3)- | H | CH3 | CH3 | CH3 | O | O |
| 253 | 3-CH3-C6H4-O-CH2-CH(CH3)- | H | CH3 | CH3 | CH3 | O | O |
| 254 | 3-Cl-C6H4-O-CH2-CH(CH3)- | H | CH3 | CH3 | CH3 | O | O |
| 255 | 3,5-(CH3)2-C6H3-O-CH2-CH(CH3)- | H | CH3 | CH3 | CH3 | O | O |
| 256 | 3-CH3-5-(CH3)2CH-C6H3-O-CH2-CH(CH3)- | H | CH3 | CH3 | CH3 | O | O |
| 257 | 2,6-(CH3)2-C6H3-O-CH2-CH(CH3)- | H | CH3 | CH3 | CH3 | O | O |
| 258 | chromane-6-O-CH2-CH(CH3)- | H | CH3 | CH3 | CH3 | O | O |
| 259 | chromane-8-O-CH2-CH(CH3)- | H | CH3 | CH3 | CH3 | O | O |

-continued
| | | | | | | |
|---|---|---|---|---|---|---|
| 260 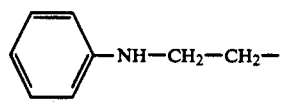 | H | CH₃ | CH₃ | CH₃ | O | O |
| 261 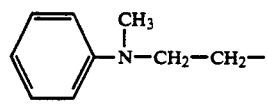 | H | CH₃ | CH₃ | CH₃ | O | O |
| 262 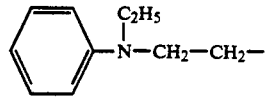 | H | CH₃ | CH₃ | CH₃ | O | O |
| 263 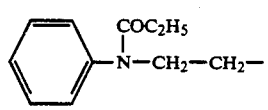 | H | CH₃ | CH₃ | CH₃ | O | O |
| 264 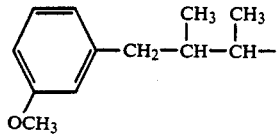 | H | CH₃ | CH₃ | CH₃ | O | O |
| 265 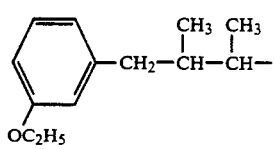 | H | CH₃ | CH₃ | CH₃ | O | O |
| 266 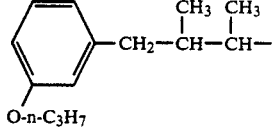 | H | CH₃ | CH₃ | CH₃ | O | O |
| 267 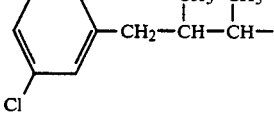 | H | CH₃ | CH₃ | CH₃ | O | O |
| 268 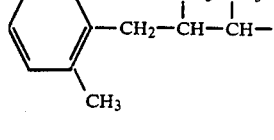 | H | CH₃ | CH₃ | CH₃ | O | O |
| 269 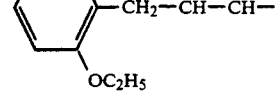 | H | CH₃ | CH₃ | CH₃ | O | O |
| 270 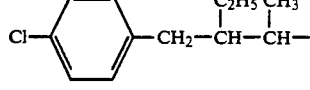 | H | CH₃ | CH₃ | CH₃ | O | O |
| 271 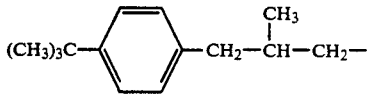 | H | CH₃ | CH₃ | CH₃ | O | O |

-continued
| | | | | | | | |
|---|---|---|---|---|---|---|---|
| 272 | 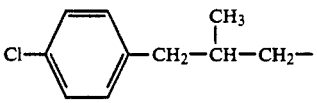 | H | CH₃ | CH₃ | CH₃ | O | O |
| 273 | 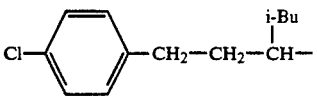 | H | CH₃ | CH₃ | CH₃ | O | O |
| 274 | 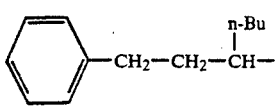 | H | CH₃ | CH₃ | CH₃ | O | O |
| 275 | 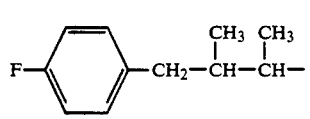 | H | CH₃ | CH₃ | CH₃ | O | O |
| 276 | 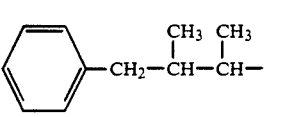 | H | CH₃ | CH₃ | CH₃ | O | O |
| 277 | 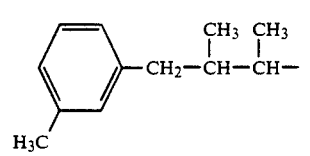 | H | CH₃ | CH₃ | CH₃ | O | O |
| 278 | 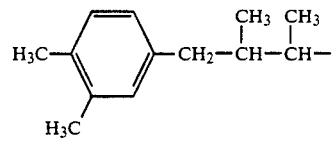 | H | CH₃ | CH₃ | CH₃ | O | O |
| 279 | 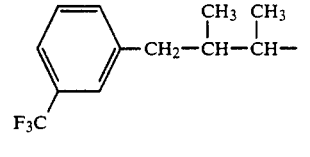 | H | CH₃ | CH₃ | CH₃ | O | O |
| 280 | 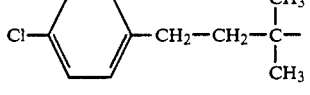 | H | CH₃ | H | CH₃ | O | O | 144 |
| 281 | 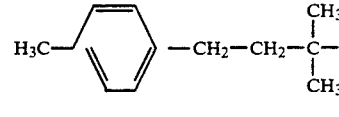 | H | CH₃ | H | CH₃ | O | O |
| 282 | 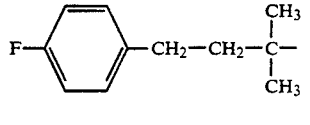 | H | CH₃ | H | CH₃ | O | O |
| 283 | 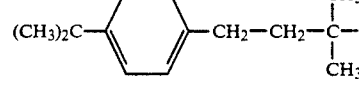 | H | CH₃ | H | CH₃ | O | O |

-continued
| | | | | | | | | |
|---|---|---|---|---|---|---|---|---|
| 284 | 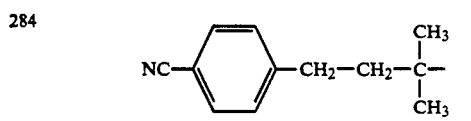 | H | CH$_3$ | H | CH$_3$ | O | O | |
| 285 | 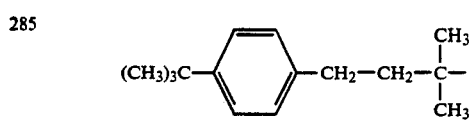 | H | CH$_3$ | H | CH$_3$ | O | O | |
| 286 | 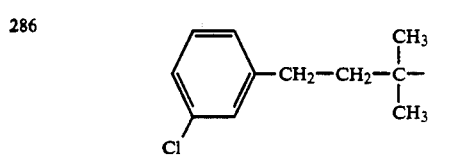 | H | CH$_3$ | H | CH$_3$ | O | O | |
| 287 | 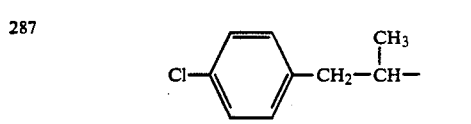 | H | CH$_3$ | H | CH$_3$ | O | O | |
| 288 | 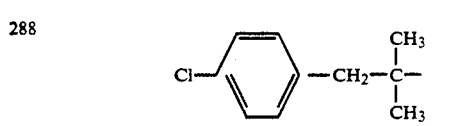 | H | CH$_3$ | H | CH$_3$ | O | O | |
| 289 | 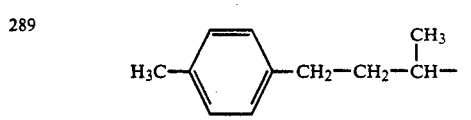 | H | CH$_3$ | H | CH$_3$ | O | O | |
| 290 | 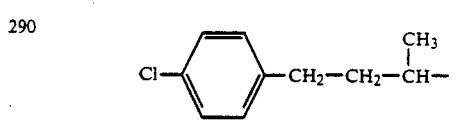 | H | CH$_3$ | H | CH$_3$ | O | O | |
| 291 | 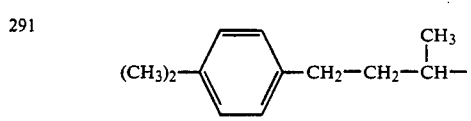 | H | CH$_3$ | H | CH$_3$ | O | O | |
| 292 | 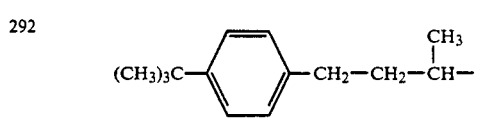 | H | CH$_3$ | H | CH$_3$ | O | O | |
| 293 | 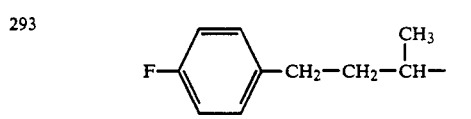 | H | CH$_3$ | H | CH$_3$ | O | O | 107 |
| 294 | 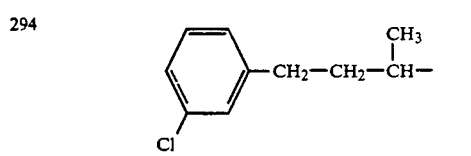 | H | CH$_3$ | H | CH$_3$ | O | O | |
| 295 | 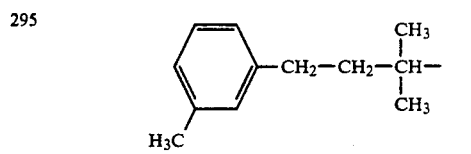 | H | CH$_3$ | H | CH$_3$ | O | O | |
| 296 | 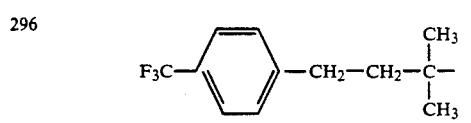 | H | CH$_3$ | H | CH$_3$ | O | O | |

-continued
| | | | | | | | |
|---|---|---|---|---|---|---|---|
| 297 | 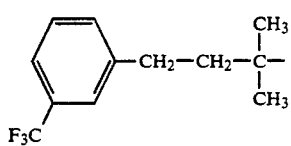 | H | CH₃ | H | CH₃ | O | O |
| 298 | 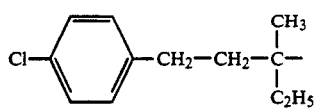 | H | H | CH₃ | CH₃ | O | O |
| 299 | 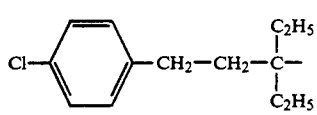 | H | H | CH₃ | CH₃ | O | O |
| 300 | 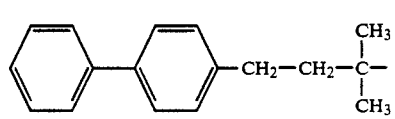 | H | CH₃ | H | CH₃ | O | O |
| 301 | 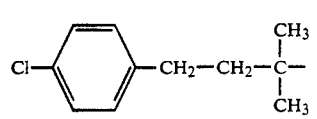 | H | CH₃ | CH₃ | CH₃ | O | O |
| 302 | 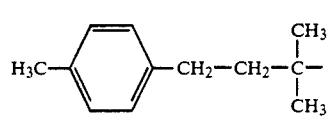 | H | CH₃ | CH₃ | CH₃ | O | O |
| 303 | 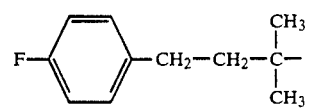 | H | CH₃ | CH₃ | CH₃ | O | O |
| 304 | 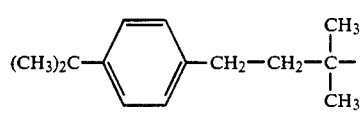 | H | CH₃ | CH₃ | CH₃ | O | O |
| 305 | 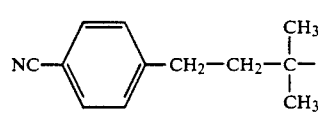 | H | CH₃ | CH₃ | CH₃ | O | O |
| 306 | 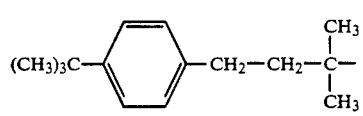 | H | CH₃ | CH₃ | CH₃ | O | O |
| 307 | 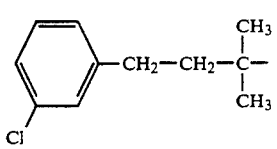 | H | CH₃ | CH₃ | CH₃ | O | O |
| 308 | 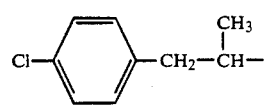 | H | CH₃ | CH₃ | CH₃ | O | O |
| 309 | 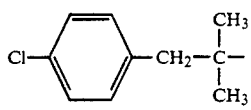 | H | CH₃ | CH₃ | CH₃ | O | O |

| | | | | | | | |
|---|---|---|---|---|---|---|---|
| 310 | 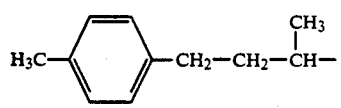 | H | CH$_3$ | CH$_3$ | CH$_3$ | O | O |
| 311 | 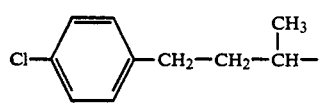 | H | CH$_3$ | CH$_3$ | CH$_3$ | O | O |
| 312 | 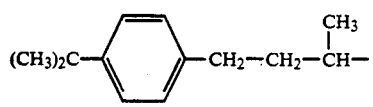 | H | CH$_3$ | CH$_3$ | CH$_3$ | O | O |
| 313 | 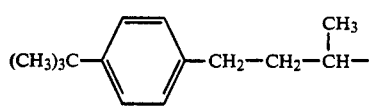 | H | CH$_3$ | CH$_3$ | CH$_3$ | O | O |
| 314 | 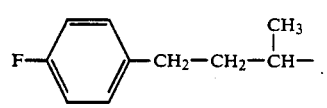 | H | CH$_3$ | CH$_3$ | CH$_3$ | O | O |
| 315 | 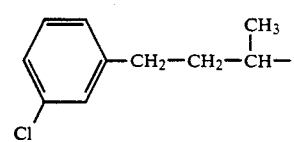 | H | CH$_3$ | CH$_3$ | CH$_3$ | O | O |
| 316 | 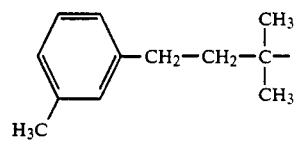 | H | CH$_3$ | CH$_3$ | CH$_3$ | O | O |
| 317 | 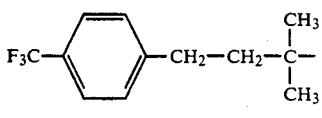 | H | CH$_3$ | CH$_3$ | CH$_3$ | O | O |
| 318 | 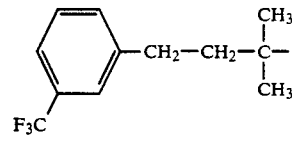 | H | CH$_3$ | CH$_3$ | CH$_3$ | O | O |
| 319 | 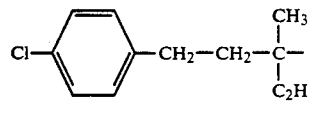 | H | CH$_3$ | CH$_3$ | CH$_3$ | O | O |
| 320 | 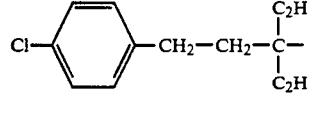 | H | CH$_3$ | CH$_3$ | CH$_3$ | O | O |
| 321 | 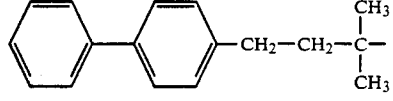 | H | CH$_3$ | CH$_3$ | CH$_3$ | O | O |

-continued

| # | Structure | | | | | | | |
|---|---|---|---|---|---|---|---|---|
| 322 | Ph-CH₂-CH(CH₃)-CH(CH₃)- | H | H | CH₃ | CH₃ | O | O | 146 |
| 323 | 4-F-C₆H₄-CH₂-CH(CH₃)-CH(CH₃)- | H | H | CH₃ | CH₃ | O | O | (amorph) |
| 324 | 3,4-F₂-C₆H₃-CH₂-CH(CH₃)-CH(CH₃)- | H | H | CH₃ | CH₃ | O | O | |
| 325 | 4-CH₃-C₆H₄-O-CH₂-CH(CH₃)- | H | H | CH₃ | CH₃ | O | O | (amorph) |
| 326 | 4-Cl-C₆H₄-CH₂-CH(C₂H₅)-CH(CH₃)- | H | H | CH₃ | CH₃ | O | O | (amorph) |
| 327 | 4-Cl-C₆H₄-CH₂-CH₂-C(CH₃)₂- | H | H | H | CH₃ | O | O | 160 |
| 328 | 4-CH₃O-C₆H₄-CH₂-CH₂-C(CH₃)₂- | H | H | H | CH₃ | O | O | 170 |
| 329 | 4-Cl-C₆H₄-CH₂-CH₂-C(CH₃)₂- | H | CH₃ | CH₃ | CH₃ | O | O | |
| 330 | 4-CH₃O-C₆H₄-CH₂-CH₂-C(CH₃)₂- | H | CH₃ | CH₃ | CH₃ | O | O | 125 |
| 331 | 4-Cl-C₆H₄-CH₂-CH₂-CH(CH₃)- | H | CH₃ | CH₃ | CH₃ | O | O | |
| 332 | 4-Cl-C₆H₄-O-CH₂-CH(CH₃)- | H | CH₃ | CH₃ | CH₃ | O | O | |
| 333 | 4-Cl-C₆H₄-CH₂-CH(CH₃)-CH(CH₃)- | H | CH₃ | CH₃ | CH₃ | O | O | |
| 334 | 4-CH₃-C₆H₄-CH₂-CH₂-CH(CH₃)- | H | CH₃ | CH₃ | CH₃ | O | O | |

-continued
| | | | | | | | | |
|---|---|---|---|---|---|---|---|---|
| 335 | 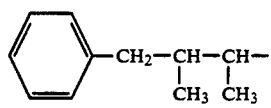 | H | CH₃ | CH₃ | CH₃ | O | O | |
| 336 | 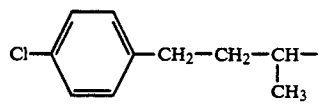 | H | H | H | CH₃ | O | O | |
| 337 | 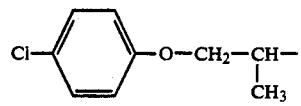 | H | H | H | CH₃ | O | O | |
| 338 | 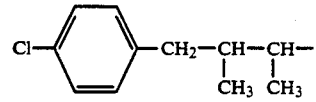 | H | H | H | CH₃ | O | O | |
| 339 | 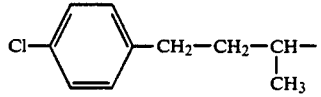 | H | H | CH₃ | CH(CH₃)₂ | O | O | 115 |
| 340 | 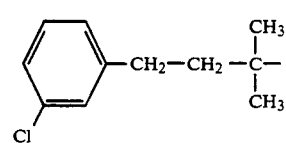 | H | H | H | CH₃ | O | O | |
| 341 | 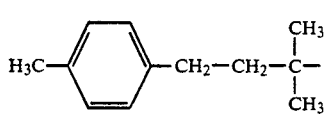 | H | CH₃ | CH₃ | CH₃ | O | O | |
| 342 | 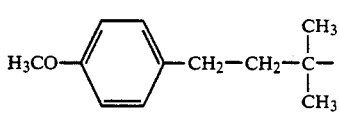 | H | H | CH₃ | CH(CH₃)₂ | O | O | |
| 343 | 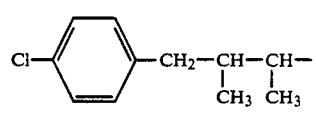 | H | H | CH₃ | CH(CH₃)₂ | O | O | |
| 344 | 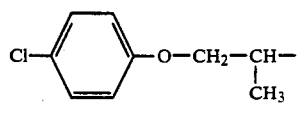 | H | H | CH₃ | CH(CH₃)₂ | O | O | |
| 345 | 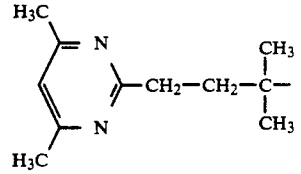 | H | CH₃ | CH₃ | CH₃ | O | O | |
| 346 | 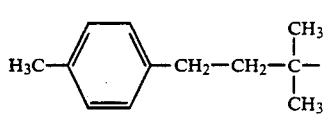 | H | H | CH₃ | CH(CH₃)₂ | O | O | |
(Expressed in terms of $CH_3$, $CH_2$, etc.)

| # | Structure | | | | | | |
|---|---|---|---|---|---|---|---|
| 347 | 4-Cl-C6H4-CH2-CH2-C(CH3)2-CH3 | H | H | CH3 | CH(CH3)2 | O | O |
| 348 | 3-Cl-C6H4-CH2-CH2-C(CH3)2-CH3 | H | H | CH3 | CH(CH3)2 | O | O |
| 349 | 4-F-C6H4-CH2-CH2-C(CH3)2-CH3 | H | H | CH3 | CH(CH3)2 | O | O |
| 350 | 4-F-C6H4-CH2-CH2-CH(CH3)- | H | H | CH3 | CH(CH3)2 | O | O |
| 351 | 4-(CH3)3C-C6H4-CH2-CH2-C(CH3)2-CH3 | H | H | H | CH3 | O | O |
| 352 | 4-Cl-C6H4-CH2-CH2-C(CH3)2-CH3 | H | H | CH3 | CH3 | O | O |
| 353 | 3-F3C-C6H4-CH2-CH2-C(CH3)2-CH3 | H | H | CH3 | CH3 | O | O | 91 |
| 354 | 2-pyridyl-CH2-CH2-C(CH3)2-CH3 | H | H | CH3 | CH3 | O | O |
| 355 | 4-Cl-C6H4-CH2-CH2-C(C2H5)2-C2H5 | H | H | CH3 | CH3 | O | O | 143 |
| 356 | 4-NC-C6H4-CH2-CH2-C(CH3)2-CH3 | H | H | CH3 | CH3 | O | O | 142 |
| 357 | 4-Cl-C6H4-O-CH2-C(CH3)2-CH(CH3)- | H | H | CH3 | CH3 | O | O | 154 |
| 358 | 3,4-Cl2-C6H3-CH2-C(CH3)2-CH(CH3)- | H | H | CH3 | CH3 | O | O | 78 |

| | | | | | | | |
|---|---|---|---|---|---|---|---|
| 359 | 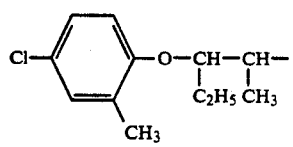 | H | H | CH₃ | CH₃ | O | O | |
| 360 | 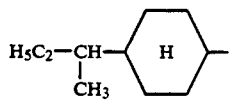 | H | H | CH₃ | CH₃ | O | O | |
| 361 | 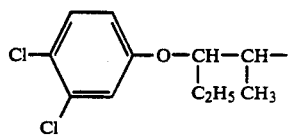 | H | H | CH₃ | CH₃ | O | O | |
| 362 | 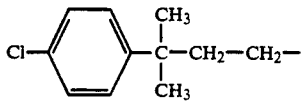 | H | H | CH₃ | CH₃ | O | O | 98 |
| 363 | 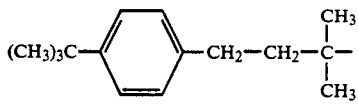 | H | H | CH₃ | CH₃ | O | O | 108 |
| 364 | 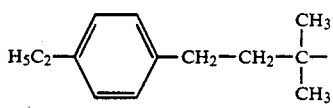 | H | H | CH₃ | CH₃ | O | O | 92 |
| 365 | 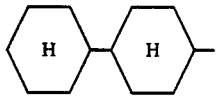 | H | H | CH₃ | CH₃ | O | O | 105 |
| 366 | 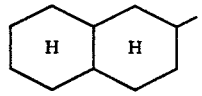 | H | H | CH₃ | CH₃ | O | O | |
| 367 | 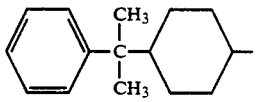 | H | H | CH₃ | CH₃ | O | O | |

STARTING SUBSTANCES OF THE FORMULAE (II)

EXAMPLE (II-1)

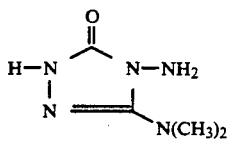

130 g (1.44 mol) of carbodihydrazide are suspended in a mixture of 470 g of phenol and 200 ml of chlorobenzene, 153 g (1.44 mol) of sodium carbonate and 3.0 g (12 mmol) of dibutyltin oxide are added and the mixture is heated to 50° C. to 60° C. in a water-jet vacuum. A solution of 247 g (1.44 mol) of tetramethylchloroformamidinium chloride in 400 g of phenol is added dropwise in the course of 20 minutes, water distilling off. Chlorobenzene is then removed by distillation in a water-jet vacuum until the boiling point of the phenol is reached. The reaction mixture is then heated to 160° C. to 180° C. under normal pressure, dimethylamine being eliminated. After 3 hours, phenol is removed by distillation at 190° C. for one hour. The solid residue which remains is extracted with 1.5 liters of isopropanol in a Soxleth extractor; the isopropanol solution is evaporated.

47 g (23% of theory) of 4-amino-5-dimethylamino-2,4-dihydro-3H-1,2,4-triazol-3-one are obtained as a crystalline residue of melting point 205° C.

EXAMPLE (II-2)

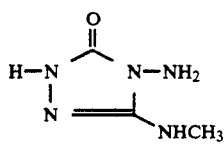

A mixture of 360 g (2.0 mol) of carbodihydrazide, 212 g (2.0 mol) of sodium carbonate and 580 g of phenol is heated to 50° C. to 60° C. A solution of 314 g (2.0 mol) of trimethyl-chloroformamidine hydrochloride in 314 g of phenol is then added dropwise in a water-jet vacuum in the course of 30 minutes. The reaction mixture is then stirred at 50° C. to 60° C. for 60 minutes and then heated to 190° C., dimethylamine being eliminated. After evolution of gas has ended, the phenol is removed by distillation in a water-jet vacuum and the residue is recrystallized from water.

60 g (26% of theory) of 4-amino-5-methylamino-2,4-dihydro-3H-1,2,4-triazol-3-one of melting point 220° C. are obtained.

EXAMPLE (II-3)

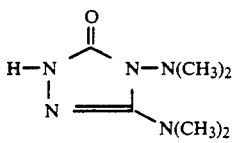

Step 1

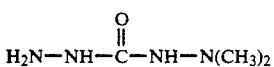 (XIIIa-1)

856 g (4.0 mol) of diphenyl carbonate are initially introduced with water cooling and 245 g (4.0 mol) of N,N-dimethylhydrazine are added dropwise. The mixture is then slowly heated to 60° C. (in the course of 4 hours). After cooling to 20° C., 200 g (4.0 mol) of hydrazine hydrate are then added to this and the reaction mixture is stirred at 20° C. for 12 hours. After heating at 70° C. to 80° C. for one hour, volatile components are removed by distillation in a water-jet vacuum up to a bottom temperature of 100° C. The residue which remains essentially contains a solution of 1,1-dimethyl-carbodihydrazide in phenol, which is employed directly for the next step.

Step 2

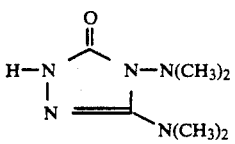 (II-3)

251 g of the above solution of 1,1-dimethyl-carbodihydrazide in phenol (about 0.82 mol) are diluted with 100 g of phenol, 87 g (0.82 mol) of sodium carbonate are added and the mixture is heated to 50° C. to 60° C. A solution of 140 g (0.82 mol) of tetramethyl-chloroformamidinium chloride in 250 g of phenol is then added dropwise in an oil pump vacuum in the course of 75 minutes. The reaction mixture is then heated at reflux temperature (about 190° C. to 195° C.) under normal pressure for 6 hours, dimethylamine being eliminated. The mixture is then distilled in an oil pump vacuum and the distillate is distilled again. The distillate then obtained (40 g) is taken up in xylene and cooled to −78° C. The product which is obtained i this process in crystalline form is isolated by filtering with suction.

22.8 g (16% of theory) of 4.5-bis-dimethylamino-2,4-dihydro-3H-1,2,4-triazol-3-one of melting point 93° C. are obtained.

EXAMPLE (II-4)

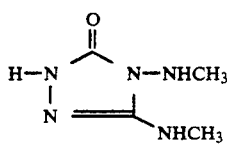

Step 1

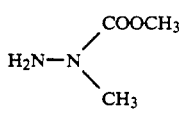 (XVIII-1)

A solution of 94 g (2.0 mol) of methylhydrazine in 100 ml of methanol is cooled to 0° C. to −20° C. and 268 g (2.0 mol) of dimethyl pyrocarbonate are continuously added dropwise such that the temperature of 0° C. is not exceeded. The reaction mixture is then stirred at 80° C. until evolution of gas has ended and is then distilled in a water-jet vacuum.

181 g (87% of theory) of N-methyl-N-methoxy-carbonylhydrazine of boiling point 65° C./15 torr are obtained.

Step 2

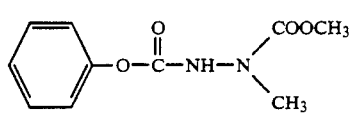 (XIX-1)

624 g (6.0 mol) of 1-methyl-1-methoxycarbonyl-hydrazine and 334 g (3.15 mol) of sodium carbonate are initially introduced into 2 liters of ethylene chloride and 939 g (6.0 mol) of phenyl chloroformate are added dropwise with stirring such that a temperature of 20° C. is not exceeded. The mixture is then stirred at 60° C. for a further 60 minutes and the sodium chloride liberated is separated off by filtering with suction. The solvent is removed from the filtrate by distillation in a water-jet vacuum at a bottom temperature of at most 110° C.

1285 g (96% of theory) of 1-methyl-1-methoxycarbonyl-2-phenoxycarbonyl-hydrazine are obtained as an oily residue which gradually crystallizes. Melting point: 86° C.

Step 3

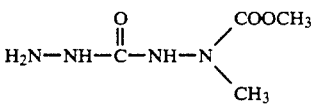 (XIIIb-1)

206 g (4.12 mol) of hydrazine hydrate are initially introduced at 20° C. and a solution of 922 g (4.12 mol) of 1-methyl-1-methoxycarbonyl-2-phenoxycarbonylhydrazine warmed to 40° C. in 600 g of chlorobenzene is added to this in a stream, whereupon the reaction mixture heats to about 60° C. The mixture is then stirred at 80° C. for 4 hours and subsequently concentrated in a water-jet vacuum to a bottom temperature of about 100° C. The residue, which essentially contains 1-methyl-1-methoxycarbonylcarbodihydrazide is employed directly for the next step.

Step 4

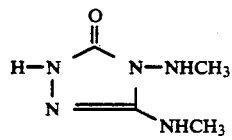
(II-4)

A mixture of 160 g (0.626 mol) of 1-methyl-1-methoxycarbonyl-carbodihydrazide and 160 g of phenol is heated to 40° C. and 142 g (0.626 mol) of diphenyl methyliminocarbonate are added. After the exothermic reaction has subsided, the mixture is slowly heated to 150° C. under a water-jet vacuum, about 150 g of phenol distilling off. After cooling, the residue is stirred with 100 ml of water and 120 g of 50% strength sodium hydroxide solution and heated under reflux for 60 minutes. 300 ml of 18% strength hydrochloric acid are then added and the mixture is evaporated. The residue is distilled in an oil pump vacuum and the crude distillate is distilled again.

45 g (50% of theory) of 4,5-bis-methylamino-2,4-dihydro-3H-1,2,4-triazol-3-one are obtained as an oily product, which solidifies in wax-like form in the receiver. After stirring with ethyl acetate, 40 g (44%) of white crystalline product of melting point 135°-137° C. are obtained.

EXAMPLE (II-5)

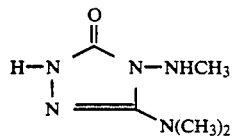

A phenolic solution of 1-methyl-1-methoxycarbonyl-carbodihydrazide is prepared as described under Example (II-4) —step 3. 384 g of this solution (1.5 mol) are taken up in 200 ml of chlorobenzene, 239 g (2.25 mol) of sodium carbonate are added and the mixture is heated to 50° C. in a water-jet vacuum. A solution of 244 g (1.5 mol) of dichloromethylene-dimethylimmonium chloride in 566 g of phenol is added dropwise during the course of this, water distilling off azeotropically. The reaction mixture is subsequently stirred under normal pressure at 120° C. for a further 60 minutes and then filtered hot and washed with ethanol and acetone. The organic solution is concentrated, and the residue is heated under reflux with 240 ml of 50% strength sodium hydroxide solution and, after cooling, neutralized with conc. hydrochloric acid. After concentrating in a water-jet vacuum, the residue is distilled in an oil pump vacuum and the crude distillate obtained in this way is distilled again.

72 g of oily product (boiling point 165° C./1 mbar) are obtained, which is converted into a pure crystalline product using 300 ml of toluene.

Yield: 60.0 g (25.5% of theory) of 4-methylamino-5-dimethylamino-2,4-dihydro-3H-1,2,4-triazol-3-one; melting point: 129° C.

EXAMPLE (II-6)

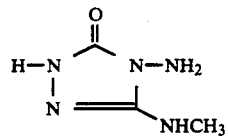

A mixture of 58 g (0.25 mol) of 1,3-diamino-2-methyl-guanidine hydroiodide, 53.5 g (0.25 mol) of diphenyl carbonate and 20 g of phenol is heated to 160° C. with stirring until the mixture has become nearly homogeneous. 34.5 g (0.25 mol) of potassium carbonate are then added to it in portions, carbon dioxide being released. After 60 minutes at 160° C., the mixture is cooled somewhat and the phenol is removed by distillation in a water-jet vacuum. The residue is taken up in 200 ml of water, neutralized with hydrochloric acid and ethanol is slowly added, the reaction mixture being obtained in crystalline form.

24 g (74% of theory) of 4-amino-5-methylamino-2,4-dihydro-3H-1,2,4-triazol-3-one of melting point 214° C. are obtained.

The compounds of the formula (II):

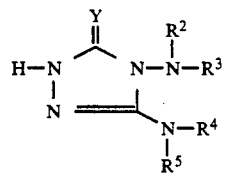
(II)

shown in Table 2 below can also be prepared analogously to Examples (II-1) to (II-6) and in accordance with the general description of the preparation processes according to the invention.

TABLE 2

Examples of the compounds of the formula (II)

| Ex. No. | $R^2$ | $R^3$ | $R^4$ | $R^5$ | Y | Melting point (°C.) |
|---|---|---|---|---|---|---|
| II-7 | H | H | $C_2H_5$ | $C_2H_5$ | O | 195-196 |
| II-8 | H | H | H | $C_2H_5$ | O | 219-220 |
| II-9 | H | H | —$(CH_2)_4$— | | O | 233 |
| II-10 | H | $CH_3$ | H | $(CH_3)_2CH$ | O | 120 |
| II-11 | H | H | H | $(CH_3)_2CH$ | O | 150-152 |
| II-12 | H | H | H | $C_3H_7$ | O | |
| II-13 | H | H | $CH_3$ | $C_2H_5$ | O | 186 |
| II-14 | H | H | $CH_3$ | $C_3H_7$ | O | 165 |
| II-15 | H | H | $CH_3$ | $(CH_3)_2CH$ | O | |
| II-16 | H | H | $C_2H_5$ | $C_3H_7$ | O | 186 |
| II-17 | H | H | $C_2H_5$ | $(CH_3)_2CH$ | O | |
| II-18 | H | H | $C_3H_7$ | $C_3H_7$ | O | |
| II-19 | H | H | $C_3H_7$ | $(CH_3)_2CH$ | O | |
| II-20 | H | $CH_3$ | $CH_3$ | $C_2H_5$ | O | |
| II-21 | H | $CH_3$ | $CH_3$ | $C_3H_7$ | O | |
| II-22 | H | $CH_3$ | $CH_3$ | $(CH_3)_2CH$ | O | |
| II-23 | H | $CH_3$ | $C_2H_5$ | $C_2H_5$ | O | |
| II-24 | H | $CH_3$ | $C_2H_5$ | $C_3H_7$ | O | |
| II-25 | H | $CH_3$ | $C_3H_7$ | $C_3H_7$ | O | |
| II-26 | H | $C_2H_5$ | $CH_3$ | $CH_3$ | O | |
| II-27 | H | $C_2H_5$ | $CH_3$ | $C_2H_5$ | O | |
| II-28 | H | $C_2H_5$ | $C_2H_5$ | $C_2H_5$ | O | |
| II-29 | H | H | —$(CH_2)_2$— | | O | |
| II-30 | H | $CH_3$ | —$(CH_2)_2$— | | O | |

TABLE 2-continued

Examples of the compounds of the formula (II)

| Ex. No. | R² | R³ | R⁴ | R⁵ | Y | Melting point (°C.) |
|---|---|---|---|---|---|---|
| II-31 | H | C₂H₅ | —(CH₂)₂— | | O | |
| II-32 | CH₃ | CH₃ | H | CH₃ | O | 167 |
| II-33 | CH₃ | CH₃ | CH₃ | C₂H₅ | O | |
| II-34 | H | H | H |  | O | |
| II-35 | H | CH₃ | H |  | O | |
| II-36 | CH₃ | CH₃ | H |  | O | |
| II-37 | H | H | CH₃ |  | O | |
| II-38 | H | CH₃ | CH₃ |  | O | 267 |

TABLE 3

Examples of the compounds of the formula (III)

| Ex. No. | R¹ | X | Physical data |
|---|---|---|---|
| III-2 | 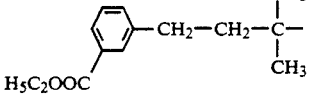 | O | |
| III-3 | 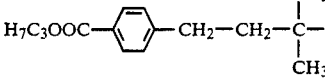 | O | B.p.: 110–113° C. at 0.008 mbar |
| III-4 | 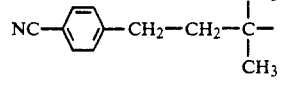 | O | B.p.: 110° C. at 0.1–0.2 mbar |
| III-5 | 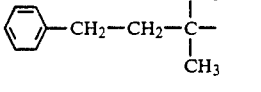 | O | |
| III-6 | 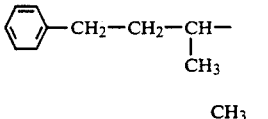 | O | |
| III-7 | 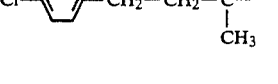 | O | B.p.: 94° C. at 0.2 mbar |
| III-8 |  | O | |
| III-9 |  | O | |
| III-10 |  | O | |
| III-11 | 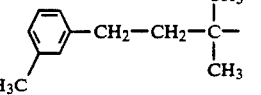 | O | |
| III-12 | 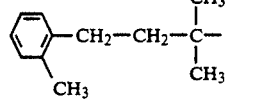 | O | |
| III-13 | 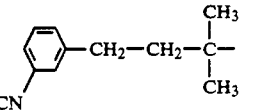 | O | |
| III-13 | 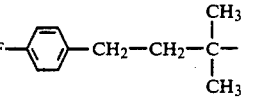 | O | |
| III-14 | 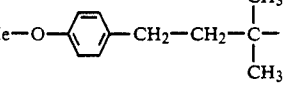 | O | |
| III-15 | 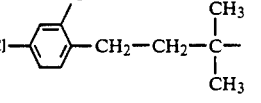 | O | |
| III-16 | 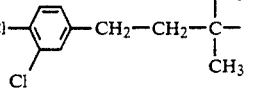 | O | |
| III-17 | 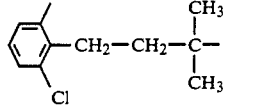 | O | |
| III-18 | 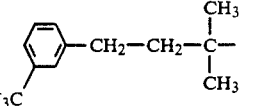 | O | |
| III-19 | 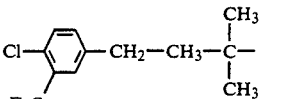 | O | |
| III-20 | F₃C—O—⟨ ⟩—CH₂—CH₂—C(CH₃)₂—CH₃ | O | |
| III-21 | 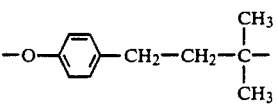 | O | |

TABLE 3-continued

Examples of the compounds of the formula (III)

| Ex. No. | R¹ | X | Physical data |
|---|---|---|---|
| III-22 | (CH₃)₃C—C₆H₄—CH₂—CH₂—C(CH₃)₂— | O | |
| III-22 | 2,5-Cl₂-C₆H₃—CH₂—CH₂—C(CH₃)₂— | O | |
| III-23 | biphenyl—CH₂—CH₂—C(CH₃)₂— | O | |
| III-24 | 3,4-(OCF₂O)-C₆H₃—CH₂—CH₂—C(CH₃)₂— | O | |
| III-25 | C₂H₅OOC—C₆H₄—CH₂—CH₂—C(CH₃)₂— | O | |
| III-26 | 3-(n-C₃H₇OOC)-C₆H₄—CH₂—CH₂—C(CH₃)₂— | O | |
| III-27 | 2-CH₃-C₆H₄—CH₂—CH₂—C(C₂H₅)(CH₃)— | O | |
| III-28 | 3-CH₃-C₆H₄—CH₂—CH₂—C(C₂H₅)(CH₃)— | O | |
| III-29 | C₆H₅—CH₂—CH₂—C(C₂H₅)₂— | O | |
| III-30 | C₆H₅—CH₂—CH₂—(1-methylcyclohexyl) | O | |
| III-31 | 4-Cl-C₆H₄—CH₂—CH₂—C(C₂H₅)(CH₃)— | O | B.p.: 98° C. at 0.7 mbar |
| III-32 | 4-Cl-C₆H₄—CH₂—CH₂—C(C₂H₅)₂— | O | |
| III-33 | C₆H₅—C≡C—C(CH₃)₂— | O | |
| III-34 | 4-Cl-C₆H₄—C≡C—C(CH₃)₂— | O | |
| III-35 | 4-NC-C₆H₄—C≡C—C(CH₃)₂— | O | |
| III-36 | 4-Cl-C₆H₄—C≡C—(1-methylcyclohexyl) | O | |
| III-37 | C₆H₅—C≡C—(1-methylcyclohexyl) | O | |
| III-38 | 4-F₂CHO-C₆H₄—C≡C—C(CH₃)₂— | O | |
| III-39 | 4-F₃CS-C₆H₄—C≡C—C(CH₃)₂— | O | |
| III-40 | 4-F₃CO-C₆H₄—CH₂—CH₂—C(CH₃)₂— | O | |
| III-41 | 4-(H₃C—CH₂)-C₆H₄—CH₂—CH₂—C(CH₃)₂— | O | |
| III-42 | 4-(CH₃)₂C-C₆H₄—CH₂—CH₂—C(CH₃)₂— | O | |
| III-43 | 4-F₂CH-C₆H₄—CH₂—CH₂—C(CH₃)₂— | O | |

STARTING SUBSTANCES OF THE FORMULA (IV):

EXAMPLE (IV-1)

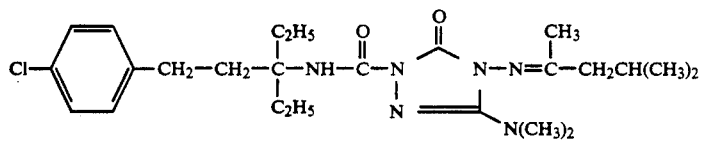

3.4 g (15 mmol) of 4-(4-methyl-2-pentylidene-amino)-5-dimethylamino-2,4-dihydro-3H-1,2,4-triazol-3-one are dissolved in 100 ml of acetonitrile and 100 mg of diazabicycloundecene (DBU) and 3.8 g (15 mmol) of 1-(4-chlorophenyl)-3-ethylpent-3-yl isocyanate are added successively. The reaction mixture is stirred at 20° C. for 2 days and then concentrated. The residue is taken up in methylene chloride, washed with water, dried using sodium sulphate and filtered. The solvent is carefully removed from the filtrate by distillation in a water-jet vacuum. The residue crystallizes on trituration with petroleum ether.

4.3 g (60% of theory) of [1-(4-chlorophenyl)-3-ethyl-pent-3-yl-aminocarbonyl]-4-(4-methyl-2-pentylideneamino)-5-dimethylamino-2,4-dihydro-3H-1,2,4-triazol-3-one of melting point 121° C. are obtained.

The compounds of the formula (IV)

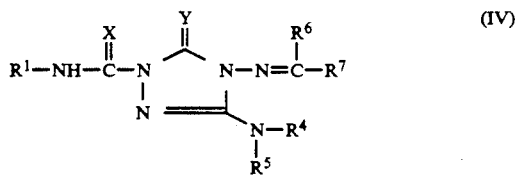

(IV)

shown in Table 4 below can also be prepared analogously to Example (IV-1) and in accordance with the general description of the preparation processes according to the invention.

TABLE 4

Examples of the compounds of the formula (IV)

| Ex. No. | $R^1$ | $R^4$ | $R^5$ | $R^6$ | $R^7$ | X | Y | M.p. (°C.) or refractive index |
|---|---|---|---|---|---|---|---|---|
| IV-2 | $FCH_2-C(CH_3)_2-$ | H | $CH_3$ | $CH_3$ | $CH_2CH(CH_3)_2$ | O | O | 88 |
| IV-3 | $FCH_2-C(CH_3)_2-$ | $CH_3$ | $CH_3$ | H | 3-Cl-phenyl | O | O | 150 |
| IV-4 | F,Cl,Br,F,CH₃-substituted group | H | $CH_3$ | $CH_3$ | $CH_2CH(CH_3)_2$ | O | O | $n_D^{20} = 1.4873$ |
| IV-5 | $ClCH_2C(CH_3)_2-$ | | $-(CH_2-)_4$ | $CH_3$ | $CH_2CH(CH_3)_2$ | O | O | $n_D^{20} = 1.5183$ |
| IV-6 | $ClCH_2C(CH_3)_2-$ | H | $CH(CH_3)_2$ | $CH_3$ | $CH_2CH(CH_3)_2$ | O | O | 48 |
| IV-7 | $FCH_2C(CH_3)_2-$ | | $-(CH_2-)_4$ | $CH_3$ | $CH_2CH(CH_3)_2$ | O | O | 115 |
| IV-8 | $C_4H_9C(CH_3)_2-$ | | $-(CH_2-)_4$ | $CH_3$ | $CH_2CH(CH_3)_2$ | O | O | $n_D^{20} = 1.4985$ |
| IV-9 | $(CH_3)_3C-CH(CH_3)-$ | | $-(CH_2-)_4$ | $CH_3$ | $CH_2CH(CH_3)_2$ | O | O | 121 |
| IV-10 | $(CH_3)_2CH-C(CH_3)_2-$ | | $-(CH_2-)_4$ | $CH_3$ | $CH_2CH(CH_3)_2$ | O | O | 73 |
| IV-11 | $(C_2H_5)_2C(CH_3)-$ | | $-(CH_2-)_4$ | $CH_3$ | $CH_2CH(CH_3)_2$ | O | O | $n_D^{20} = 1.5115$ |
| IV-12 | cyclohexyl(H)(C₂H₅)- | | $-(CH_2-)_4$ | $CH_3$ | $CH_2CH(CH_3)_2$ | O | O | $n_D^{20} = 1.5163$ |
| IV-13 | cyclopentyl- | | $-(CH_2-)_4$ | $CH_3$ | $CH_2CH(CH_3)_2$ | O | O | 112 |
| IV-14 | $C_6H_5-O-CH(CH_3)CH_2-$ | | $-(CH_2-)_4$ | $CH_3$ | $CH_2CH(CH_3)_2$ | O | O | 88 |

TABLE 4-continued

Examples of the compounds of the formula (IV)

| Ex. No. | R¹ | R⁴ | R⁵ | R⁶ | R⁷ | X | Y | M.p. (°C.) or refractive index |
|---|---|---|---|---|---|---|---|---|
| IV-15 | 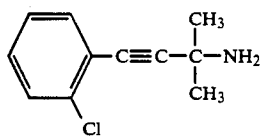 | | —(CH₂—)₄ | CH₃ | CH₂CH(CH₃)₂ | O | O | $n_D^{20} = 1.5100$ |
| IV-16 | C₂H₅C(CH₃)₂— | | —(CH₂—)₄ | CH₃ | CH₂CH(CH₃)₂ | O | O | $n_D^{20} = 1.5016$ |
| IV-17 | C₂H₅—CH—<br>\|<br>CH₃ | | —(CH₂—)₄ | CH₃ | CH₂CH(CH₃)₂ | O | O | $n_D^{20} = 1.5095$ |
| IV-18 | (CH₃)₃C— | | —(CH₂—)₄ | CH₃ | CH₂CH(CH₃)₂ | O | O | 117 |
| IV-19 | nC₄H₉ | | —(CH₂—)₄ | CH₃ | CH₂CH(CH₃)₂ | O | O | $n_D^{20} = 1.5130$ |
| IV-20 | HC≡C—C(CH₃)₂— | | —(CH₂—)₄ | CH₃ | CH₂CH(CH₃)₂ | O | O | 101 |
| IV-21 | (CH₃)₂CHCH—<br>\|<br>CH₃ | | —(CH₂—)₄ | CH₃ | CH₂CH(CH₃)₂ | O | O | 76 |
| IV-22 | (CH₃)₃C— | | —CH₂CH₂OCH₂CH₂— | CH₃ | CH₂CH(CH₃)₂ | O | O | 110 |
| IV-23 | ClCH₂C(CH₃)₂— | CH₃ | CH₃ | CH₃ | CH₂CH(CH₃)₂ | O | O | $n_D^{20} = 1.5095$ |
| IV-24 | F—⌬—CH—CH—CH—<br>      \|    \|<br>     CH₃ CH₃ | CH₃ | CH₃ | CH₃ | CH₂CH(CH₃)₂ | O | O | amorphous |
| IV-25 | H₃C—⌬—CH₂—CH₂—C(CH₃)₂—CH₃ | H | CH₃ | CH₃ | CH₂CH(CH₃)₂ | O | O | 135 |

STARTING SUBSTANCES OF THE FORMULA (VI):

EXAMPLE (VI-1)

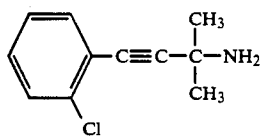

96.7 g (0.50 mol) of 1-bromo-2-chloro-benzene and 45.7 g (0.55 mol) of 3-amino-3,3-dimethyl-1-propine are initially introduced into 500 ml of triethylamine. After adding 7.0 g (0.01 mol) of palladium(II)-bis(triphenylphosphine) dichloride, 7.6 g (0.04 mol) of copper(I) iodide and 21.0 g (0.4 mol) of triphenylphosphine, the reaction mixture is heated to reflux for 24 hours. It is then filtered and the filtrate is concentrated in a water-jet vacuum. The residue is extracted with methylene chloride/water (about 300 ml/300 ml), and the organic phase is separated off, dried using sodium sulphate and filtered. The solvent is removed from the filtrate by distillation in a water-jet vacuum and the crude product which remains is purified by distillation in an oil pump vacuum.

74.1 g (75% of theory) of 3-amino-3,3-dimethyl-1-(2-cloro-phenyl)-1-propine of refractive index $n_D^{21} = 1.5799$ are obtained.

EXAMPLE (VI-2)

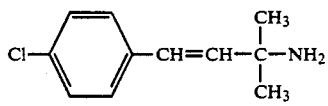

96.8 g (0.50 mol) of 3-amino-3,3-dimethyl-1-(4-chlorophenyl)-1-propine are mixed with 400 ml of tetrahydrofuran in a Parr hydrogenation apparatus and 13.0 g of Lindlar catalyst (5% palladium on calcium carbonate doped with lead) are added. The mixture is then shaken under a hydrogen pressure of 3 bar at a temperature alighting gradually from 25° C. to 50° C. until the calculated uptake of hydrogen is complete (1 mol equivalent after about 15 hours). The mixture is then filtered, the filtrate is concentrated in a water-jet vacuum and the crude product which remains is purified by distillation in an oil pump vacuum.

67.5 g (69% of theory) of 3-amino-3,3-dimethyl-1-(4-chloro-phenyl)-1-propene of refractive index $n_D^{21} = 1.5528$ are obtained.

EXAMPLE (VI-3)

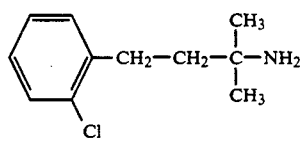

40.6 g (0.21 mol) of 3-amino-3,3-dimethyl-1-(2-chlorophenyl)-1-propine are mixed with 250 ml of tetrahydrofuran in a stirred autoclave and 10 g of Raney nickel are added. Hydrogen is then metered in up to a pressure of 50 bar and the mixture is gradually warmed from 25° C. to 40° C. with stirring. The hydrogen pressure is in each case adjusted repeatedly to 50 bar after falling to 40 bar until the pressure remains constant. The mixture is then filtered, the filtrate is concentrated in a water-jet vacuum and the crude product which remains is distilled in an oil pump vacuum.

31.8 g (77% of theory) of 3-amino-3,3-dimethyl-1-(2-chloro-phenyl)-propane of refractive index $n_D^{21} = 1.4817$ are obtained.

The compounds of the formula (VI)

$$R^1-NH_2 \quad (V)$$

shown in Table 5 below can also be prepared, for example, analogously to Examples (VI-1) to (VI-3).

TABLE 5

| Examples of the compounds of the formula (IV) | | |
|---|---|---|
| Ex. No. | $R^1$ | Physical data |
| VI-4 | C₆H₅–CH₂–CH₂–C(CH₃)₂– | |
| VI-5 | 4-Cl-C₆H₄–CH₂–CH₂–CH(CH₃)– | |
| VI-6 | C₆H₅–CH₂–CH₂–CH(CH₃)– | |
| VI-7 | 4-H₃CO-C₆H₄–CH₂–CH₂–C(CH₃)₂– | |
| VI-8 | 4-(CH₃)₂N-C₆H₄–CH₂–CH₂–C(CH₃)₂– | |
| VI-9 | 4-F-C₆H₄–CH₂–CH₂–C(CH₃)₂– | |
| VI-10 | C₆H₅–CH₂–CH₂–C(CH₃)(C₂H₅)– | |
| VI-11 | 3,4-(H₃CO)₂-C₆H₃–CH₂–CH₂–CH(CH₃)– | |
| VI-12 | 4-(CH₃)₂N-C₆H₄–CH₂–CH₂–CH(CH₃)– | |
| VI-13 | C₆H₅–CH₂–CH₂–CH(C₂H₅)– | |
| VI-14 | 4-H₃C-C₆H₄–CH₂–CH₂–CH(CH₃)– | |
| VI-15 | 3-H₃CO-C₆H₄–CH₂–CH₂–CH(CH₃)– | |
| VI-16 | C₆H₅–CH=CH–CH(CH₃)– | |
| VI-17 | C₆H₅–C≡C–CH(CH₃)– | |
| VI-18 | C₆H₅–C≡C–C(CH₃)₂– | |
| VI-19 | 4-Cl-C₆H₄–CH₂–CH₂–C(C₂H₅)₂– | |
| VI-20 | 4-Cl-C₆H₄–CH₂–CH₂–C(cyclohexyl)– | |

STARTING SUBSTANCES OF THE FORMULA (VIII)

EXAMPLE (VIII-1)

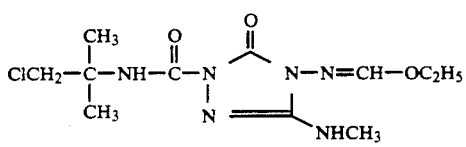

3.7 g (0.02 mol) of 4-ethoxymethyleneamino-5-methylamino-2,4-dihydro-3H-1,2,4-triazol-3-one are dissolved in 100 ml of acetonitrile and 100 mg of diazabicycloundecene (DBU) and 2.8 g (0.02 mol) of chloro-tert-butyl isocyanate are added successively. The mixture is stirred at 20° C. for 12 hours and then concentrated. The residue is taken up in methylene chloride, washed with water, dried using sodium sulphate and filtered. The solvent is removed from the filtrate by distillation in a water-jet vacuum and the residue is crystallized by trituration with diethyl ether.

5.2 g (82% of theory) of 2-chloro-tert-butyl-aminocarbonyl-4-ethoxymethyleneamino-5-methylamino-2,4-dihydro-3H-1,2,4-triazol-3-one of melting point 142° C. are obtained.

The compounds of the formula (VIII)

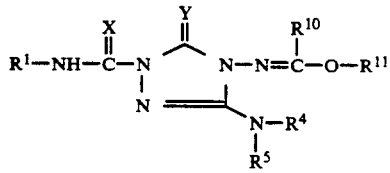
(VIII)

shown in Table 6 below can also be prepared analogously to Example VIII-1 and in accordance with the general description of the preparation processes according to the invention.

(XXI)

shown in Table 7 below can also be prepared analogously to Example (XXI-1) and in accordance with the general description of the preparation processes according to the invention.

TABLE 7

| Examples of the compounds of the formula (XXI) | | | | | |
|---|---|---|---|---|---|
| Ex. No. | $R^4$ | $R^5$ | $R^6$ | $R^7$ | Y | M.p. (°C.) |
| XXI-2 | $CH_3$ | $CH_3$ | $CH_3$ | $CH_3$ | O | 197 |
| XXI-3 | $CH_3$ | $CH_3$ | $CH_3$ | $(CH_3)_2CH-CH_2-$ | O | 105 |
| XXI-4 | $-(CH_2)_4-$ | | $CH_3$ | $(CH_3)_2CH-CH_2-$ | O | 133 |
| XXI-5 | H | $C_2H_5$ | $CH_3$ | $(CH_3)_2CH-CH_2-$ | O | 105 |
| XXI-6 | H | $(CH_3)_2CH$ | $CH_3$ | $(CH_3)_2CH-CH_2-$ | O | 94 |
| XXI-7 | H | $C_3H_7$ | $CH_3$ | $(CH_3)_2CH-CH_2-$ | O | |
| XXI 8 | $CH_3$ | $C_2H_5$ | $CH_3$ | $(CH_3)_2CH-CH_2-$ | O | |
| XXI-9 | $C_2H_5$ | $C_2H_5$ | $CH_3$ | $(CH_3)_2CH-CH_2-$ | O | 80 |
| XXI-10 | $CH_3$ | $C_3H_7$ | $CH_3$ | $(CH_3)_2CH-CH_2-$ | O | |

TABLE 6

| Examples of the compounds of the formula (VIII) | | | | | | | |
|---|---|---|---|---|---|---|---|
| Ex. No. | $R^1$ | $R^4$ | $R^5$ | $R^{10}$ | $R^{11}$ | X | Y | M.p. (0° C.) |
| VIII-2 | $(CH_3)_3C-$ | $CH_3$ | $CH_3$ | H | $C_2H_5$ | O | O | |
| VIII-3 | $(CH_3)_3C-$ | $C_2H_5$ | $C_2H_5$ | H | $C_2H_5$ | O | O | |
| VIII-4 | $Cl-CH_2-C(CH_3)_2-$ | $CH_3$ | $CH_3$ | H | $C_2H_5$ | O | O | |
| VIII-5 | cyclopentyl | $-(CH_2)_4-$ | | H | $C_2H_5$ | O | O | |
| VIII-6 | $Cl-CH_2-C(CH_3)_2-$ | $-CH(CH_3)_2-$ | | H | $C_2H_5$ | O | O | |

INTERMEDIATES O THE FORMULA (XXI):

EXAMPLE (XXI-1)

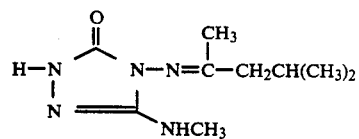

12.9 g (0.1 mol) of 4-amino-5-methylamino-2,4-dihydro-3H-1,2,4-triazol-3-one are heated under reflux in a water separator with 150 ml of methyl isobutyl ketone and 100 mg of p-toluenesulphonic acid until virtually no more water is separated (about 2 hours). The mixture is filtered, the filtrate is concentrated and the residue is triturated with petroleum ether.

8.3 g (39% of theory) of 4-(4-methyl-2-pentylideneamino)-5-methylamino-2,4-dihydro-3H-1,2,4-triazol-3-one of melting point 136° C. are obtained.

The compounds of the formula (XXI):

INTERMEDIATES OF THE FORMULA (XXV):

EXAMPLE (XXV-1)

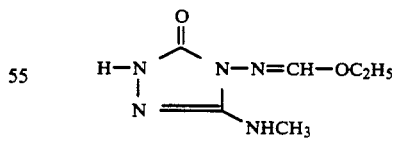

12.9 g (0.1 mol) of 4-amino-5-methylamino-2,4-dihydro-3H-1,2,4-triazol-3-one are heated to reflux for 4 hours with 100 ml of triethyl orthoformate and 100 mg of p-toluenesulphonic acid. The mixture is then concentrated and the residue is crystallized using diethyl ether. After recrystallization from ethanol, 10.0 g (54% of theory) of -ethoxymethyleneamino-5-methylamino-2,4-dihydro-3H-1,2,4-triazol-3-one of melting point 169° C. are obtained.

The compounds of the formula (XXV):

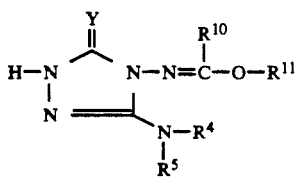

(XXV)

shown in Table 8 below can also be prepared analogously to Example (XXV-1) and in accordance with the general description of the preparation processes according to the invention.

TABLE 8

| Examples of the compounds of the formula (XXV) | | | | | |
|---|---|---|---|---|---|
| Ex. No. | $R^4$ | $R^5$ | $R^{10}$ | $R^{11}$ | Y | M.p. (°C.) |
| XXV-2 | $CH_3$ | $CH_3$ | H | $C_2H_5$ | O | 72 |
| XXV-3 | $CH_3$ | $C_2H_5$ | H | $C_2H_5$ | O | |
| XXV-4 | $CH_3$ | $C_3H_7$ | H | $C_2H_5$ | O | |
| XXV-5 | H | $CH_3$ | $CH_3$ | $C_2H_5$ | O | |
| XXV-6 | —($CH_2$)$_4$— | | H | $C_2H_5$ | O | |
| XXV-7 | $C_2H_5$ | $C_2H_5$ | H | $C_2H_5$ | O | |
| XXV-8 | H | $CH(CH_2)_2$ | H | $C_2H_5$ | O | |

USE EXAMPLES

In the following use examples, the compound shown below was used as a comparison substance:

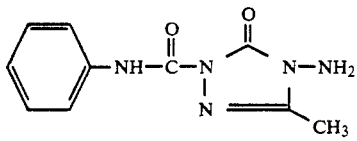

(A)

4-Amino-5-methyl-2-phenylaminocarbonyl-2,4-dihydro-3H-1,2,4-triazol-3-one (known from EP-A 294,666, Example 122).

EXAMPLE A

| Post-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control.

The figures denote:
0% = no action (like untreated control)
100% = total destruction
In this test, for example, the compounds according to the following preparation examples: 1, 2, 6, 7, 15, 16, 17, 18, 20, 21, 22, 23, 24, 25, 26, 27, 28, 30, 46, 50, 52, 53, 54, 55, 56, 57, 58, 59, 60, 61, 62, 63, 66, 71, 72, 73, 76, 77, 78, 79, 81, 82, 84, 85 and 87 show a clearly superior activity compared to the prior art.

EXAMPLE B

| Defoliation and desiccation of the leaves of cotton | |
|---|---|
| Solvent: | 30 parts by weight of dimethylformamide |
| Emulsifier: | 1 part by weight of polyoxyethylene sorbitan monolaurate |

To produce a suitable preparation of active compound, 1 part by weight of active compound is mixed with the stated amounts of solvent and emulsifier and the mixture is made up to the desired concentration with water.

Cotton plants are grown in a greenhouse until the 5th true leaf has unfolded completely. In this stage, the plants are sprayed with the preparations of active compound until dripping wet. After 1 week, the shedding of leaves and the desiccation of the leaves are rated, in comparison with the control plants.

In this test, for example, the compounds according to Preparation Example 15 and 16 show severe defoliation and desiccation of the leaves on cotton.

It is understood that the specification and examples are illustrative but not limitative of the present invention and that other embodiments within the spirit and scope of the invention will suggest themselves to those skilled in the art.

What is claimed is:

1. A substituted 4,5-diamino-1,2,4-triazol-3-(thi)one of the formula

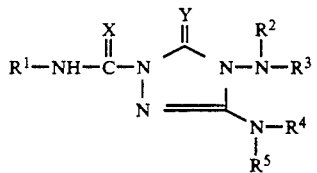

(I)

in which $R^1$ represents in each case straight-chain or branched alkyl having 1 to 18 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 2 to 8 carbon atoms and 1 to 13 identical or different halogen atoms, cyanoalkyl having 1 to 8 carbon atoms, hydroxyalkyl having 1 to 8 carbon atoms and 1 to 6 hydroxyl groups, or phenoxyalkyl, phenylthioalkyl, phenylsulphinylalkyl, phenylsulphonylalkyl, phenylaminoalkyl or N-($C_1$-$C_4$-alkyl)-phenylaminoalkyl in each case having 1 to 4 carbon atoms in the alkyl moiety, alkoxyalkyl, alkoxycarbonylalkyl or alkoxycarbonylalkenyl in each case having 1 to 6 carbon atoms in the individual alkyl and alkenyl moieties, alkylaminoalkyl or dialkylaminoalkyl in each case having 1 to 6 carbon atoms in the individual alkyl moieties, or cycloalkyl, cycloalkylalkyl, cycloalkenyl or cycloalkenylalkyl in each case having 3 to 8 carbon atoms in the cycloalkyl or cycloalkenyl moiety and if appropriate 1 to 6 carbon atoms in the alkyl moiety and in each case optionally monosubstituted to trisubstituted by identical or different substituents selected from the group consisting of halogen, cyano, phenyl, cyclohexyl, phenylethyl, phenylisopropyl and straight-chain or branched alkyl or halogenoalkyl having 1 to 4 carbon atoms and if appropriate 1 to 9 identical or different halogen atoms and straight-chain or branched halogenoalkenyl having 1 to 4 carbon atoms and 1 to 5 identical or different halogen atoms or doubly linked alkanediyl, or alkenedyl having up to 4 carbon atoms; $R^1$ additionally represents in each case straight-chain or branched alkoxy having 1 to 8 carbon atoms, alkenyloxy having 2 to 8 carbon aoms or alkinyloxy having 2 to 8 carbon atoms or represents aralkyl, arylalkenyl, arylalkinyl, aroyl, aryl, aralkyloxy or aryloxy, in each case having 6 to 10 carbon atoms in the aryl moiety and if appropriate 1 to 8 carbon atoms in the straight-cain or branched alkyl moiety or 2 to 8 carbon atoms in the straight-chain or branched alkenyl moiety or alkinyl moiety and optionally monosubstituted to trisubstituted by identical or different substituents, it being possible for the hydrogen atoms of the α-carbon atom to be replaced by ethane-1,2-diyl, propane-1,3-diyl, butane-1,4-diyl or pentane-1,5-diyl, the alkyl substituents when present being halogen or cyano and the aryl substituents when present being selected from the group consisting of halogen, cyano, nitro, amino, hydroxyl, alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl having 1 to 6 carbon atoms in the alkyl moiety and if appropriate 1 to 9 identical or different halogen atoms, cycloalkyl having 3 to 6 carbon aoms and phenoxy; or $R^1$ represents benzyl having an —O—CH$_2$—O— group fused to the phenyl moiety, $R^2$, $R^3$, $R^4$ and $R^5$ are identical or different and independently of one another represent hydrogen, or in each case case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 2 to 8 carbon atoms and 1 to 13 identical or different halogen atoms, cyanoalkyl having 1 to 8 carbon atoms, alkoxyalkyl or alkylthioalkyl having up to 4 carbon atoms in the individual alkyl moieties, or cycloalkyl or cycloalkylalkyl having 3 to 8 carbon atoms in the cycloalkyl moiety and if appropriate 1 to 6 carbon atoms in the alkyl moiety and optionally monosubstituted to trisubstituted by identical or different substituents selected from the group consisting of halogen, cyano and straight-chain or branched alkyl or halogenoalkyl having 1 to 4 carbon atoms and if appropriate 1 to 9 identical or different halogen atoms, the radicals $R^2$ to $R^5$ further represent aryl or aralkyl having 6 or 10 carbon atoms in the aryl moiety and if appropriate 1 to 4 carbon aoms in the straight-chain or branched alkyl moiety and optionally monosubstituted to trisubstituted by identical or different substituents selected from the group consisting of halogen, cyano, nitro, hydroxyl, alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl having 1 to 6 carbon atoms in the alkyl moiety and if appropriate 1 to 9 halogen atoms, in which additionally two of these radicals —$R^2$ and $R^3$ or $R^4$ and $R^5$—can also together represent straight-chain or branched alkanediyl having 2 to 6 carbon atoms, and $R^5$ can also represent straight-chain or ranched alkoxy having 1 to 8 carbon aoms, X represnts oxygen or sulphur and Y represents oxygen or sulphur.

2. A substituted 4,5-diamino-1,2,4-triazol-3-(thi)one according to claim 1, in which $R^1$ represents methyl, ethyl, n- or i-propyl, n-, i-, s- or t-butyl, straight-chain or branched pentyl, hexyl, heptyl, octyl, nonyl, decyl, dodecyl, or allyl, straight-chain or branched butenyl, pentenyl or hexenyl, propargyl, straight-chain or branched butinyl, pentinyl or hexinyl, or straight-chain or branched halogenoalkyl having 1 to 8 carbon atoms and 1 to 9 identical or different halogen atoms, or straight-chain or branched halogenoalkenyl or halogenoalkinyl having 3 to 8 carbon atoms and 1 to 3 halogen atoms, or straight-chain or branched cyanoalkyl having 1 to 6 carbon atoms in the alkyl moiety, hydroxyalkyl having 1 to 6 carbon atoms and 1 to 3 hydroxyl groups, alkoxyalkyl, alkoxycarbonylalkyl or alkoxycarbonylalkenyl, alkylaminoalkyl or dialkylaminoalkyl having up to 4 carbon atoms in the individual alkyl or alkenyl moieties or represents cyclopropyl, cyclopropylmethyl, cyclopropylethyl, cyclopentyl, cyclohexyl, cycloheptyl, cyclooctyl, cyclohexylmethyl, cyclohexylethyl, cyclohexenyl or cyclohexenylmethyl which are optionally monosubstituted to trisubstituted by identical or different substituents selected from the group consisting of fluorine, chlorine, bromine, methyl, ethyl, n- or i-propyl, n-, i-, s- or t-butyl, cyano, methanediyl, ethanediyl, butanediyl, butadienediyl and dichloroallyl;

$R^1$ additionally represents straight-chain or branched alkoxy having 1 to 6 carbon atoms, alkenyloxy having 3 to 6 carbon atoms or alkinyloxy having 3 to 6 carbon atoms or represents optionally straight-chain or branched benzyl, phenylethyl, phenylpropyl, phenylpropenyl, phenylpropinyl, phenylbutyl, phenylbutenyl, phenylbutinyl, phenylpentyl, phenylpentenyl, phenylpentinyl, phenylhexyl, phenylhexenyl, phenylhexinyl, phenylheptyl, phenylheptenyl, phenylheptinyl, phenyloctyl, phenyloctenyl, phenyloctinyl, phenylcyanomethyl, phenylcyanoethyl, phenylcyanopropyl, benzyloxy, phenylethyloloxy, phenoxy, phenoxyethyl, phenoxypropyl, phenoxy-i-propyl, phenoxyisobutyl, phenoxy-tert-butyl, phenylthioisobutyl, phenylthiotert-butyl, phenylthioethyl, phenylthiopropyl, phenylthio-i-propyl, benzoyl, phenyl or naphthyl which are optionally monosubstituted to trisubstituted by identical or different substituents selected from the group consisting of fluorine, chlorine, bromine, hydroxyl, cyano, nitro, methyl, ethyl, n- or i-propyl, n-, i-, s- or t-butyl, methoxy, ethoxy, methylthio, difluoromethyl, trifluoromethyl, difluoromethoxy, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, n- or i-propoxycarbonyl, cyclohexyl and phenoxy, $R^2$ represnts hydrogen, methyl, ethyl, propyl, isopropyl, butyl, isobutyl, sec-butyl, allyl, propargyl, cyanoethyl, methoxyethyl, cyclopropyl, cyclopentyl, cyclohexyl, phenyl or benzyl, $R^3$ represents hydrogen, methyl, ethyl, propyl, butyl, allyl, propargyl, cyanoethyl, methoxyethyl or benzyl which is optionally substituted by chlorine, or together with $R^2$ represents butane-1,4-diyl or pentane-1,5-diyl, $R^4$ represents hydrogen, methyl, ethyl, propyl, isopropyl, butyl, isobutyl, sec-butyl, allyl, propargyl, cyanoethyl, methoxethyl, cyclopropyl, cyclopentyl, cyclohexyl, phenyl or benzyl, $R^5$ represents hydrogen, methyl, ethyl, propyl, butyl, allyl, propargyl, cyanoethyl, methoxyethyl, methoxy or benzyl, or together with $R^4$ represnts butane-1,4-diyl or pentane-1,5-diyl, X represents oxygen or sulphur and
Y represents oxygen or sulphur.

3. A substituted 4,5-diamino-1,2,4-triazol-3-(thi)one according to claim 1, in which $R^1$ represents 1-methyl-3-phenyl-propyl, 1-ethyl-3-phenyl-propyl, 1-propyl-3-phenyl-propyl, 1-isopropyl-3-phenyl-propyl, 2-methyl-3-phenylpropyl, 1,1-dimethyl-3-phenyl-propyl, 1-methyl-1-ethyl-3-phenyl-propyl, 1,1-diethyl-3-phenylpropyl, 1-methyl-1-propyl-3-phenyl-propyl, 1-methyl-3-phenyl-2-propenyl, 1-ethyl-3-phenyl-2-propenyl, 1-propyl-3-phenyl-2-propenyl, 1-isopropyl-3-phenyl-2-propenyl, 1,1-dimethyl-3-phenyl-2-propenyl, 1-methyl-1-ethyl-3-phenyl-2-propenyl, 1,1-diethyl-3-phenyl-2-propenyl, 1-methyl-1-propyl-3-phenyl-2-propenyl, 1-methyl-3-phenyl-2-propinyl, 1-ethyl-3-phenyl-2-propinyl, 1-propyl-3-phenyl-2-propinyl, 1-isopropyl-3-phenyl-2-propinyl, 1,1-dimethyl-3-phenyl-2-propinyl, 1-methyl-1-ethyl-3-phenyl-2-propinyl, 1,1-diethyl-3-phenyl-2-propinyl, 1-methyl-1-propyl-3-phenyl-2-propinyl, 1,2-dimethyl-3-phenyl-propyl, 2-ethyl-1-methyl-3-phenyl-propyl, 1,2,2-trimethyl-3-phenyl-propyl, 1,3,3-trimethyl-3-phenyl-propyl or 1,1,2,2-tetramethyl-3-phenyl-propyl which a optionally monosubstituted to trisubstituted by identical or different substituents selected form the group consisting of fluorine, chlorine, bromine, methyl, ethyl, n- or i-propyl, n-, i-, s- or t-butyl, trifluoromethyl, phenyl, methoxy, ethoxy, propoxy, isopropoxy, difluoromethoxy, trifluoromethoxy, difluoromethyl, methoxycarbonyl, ethoxycarbonyl, propoxycarbonyl, cyano, methylthio, ethylthio, propylthio, isopropylthio, difluoromethylthio, trifluoromethylthio, methylsulphinyl, methylsulphonyl and trifluoromethylsulphonyl, furthermore $R^2$ represents hydrogen,
$R^3$ represents hydrogen or methyl,
$R^4$ represents hydrogen, methyl or ethyl, $R^5$ represents hydrogen, methyl, ethyl, n- or isopropyl, or $R^4$ and $R^5$ together represent butane-1,4-diyl, X represents oxygen or sulphur and
Y represents oxygen.

4. The 4,5-diamino-1,2,4-triazol-3-one derivative according to claim 1, having the formula 5. The 4,5-diamino-1,2,4-triazol-3-one derivative according to claim 1, having the formula 6. The 4,5-diamino-1,2,4-triazol-3-one derivative according to claim 1, having the formula 7. The 4,5-diamino-1,2,4-triazol-3-one derivative according to claim 1, having the formula 8. The 4,5-diamino-1,2,4-triazol-3-one derivative according to claim 1, having the formula 9. A herbicidal composition comprising a herbicidally effective amount of a compound according to claim 1 and a diluent.

10. A method of combating unwanted vegetation which comprises administering to such vegetation or to a locus from which it is desired to exclude such vegetation a herbicidally effective amount of a compound according to claim 1.

11. The method according to claim 10, wherein the 4,5-diamino-1,2,4-triazol-3-(thi)one is selected from the group consisting of

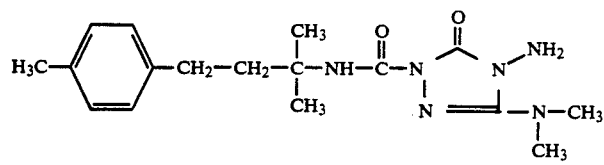
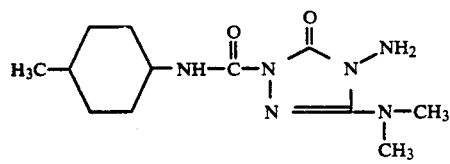
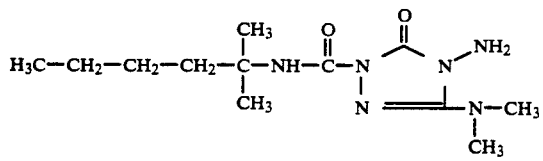
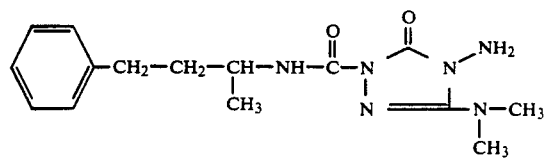
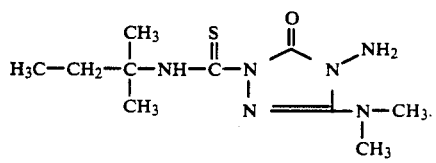
* * * * *

UNITED STATES PATENT AND TRADEMARK OFFICE
CERTIFICATE OF CORRECTION

PATENT NO. : 5,276,008
DATED : January 4, 1994
INVENTOR(S) : Kuhnt, et al.

It is certified that error appears in the above-indentified patent and that said Letters Patent is hereby corrected as shown below:

Col. 111, line 54   Delete " a " and substitute -- are --

Col. 111, line 56   Delete " form " and substitute -- from --

Signed and Sealed this

Twenty-ninth Day of August, 1995

Attest:

BRUCE LEHMAN

*Attesting Officer*   *Commissioner of Patents and Trademarks*